United States Patent
Zhang et al.

(10) Patent No.: US 10,814,140 B2
(45) Date of Patent: Oct. 27, 2020

(54) SYSTEMS AND METHODS FOR VISUALIZING AND CONTROLLING OPTOGENETIC STIMULATION USING OPTICAL STIMULATION SYSTEMS

(71) Applicant: Boston Scientific Neuromodulation Corporation, Valencia, CA (US)

(72) Inventors: Tianhe Zhang, Studio City, CA (US); Rosana Esteller, Santa Clarita, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 229 days.

(21) Appl. No.: 16/017,601

(22) Filed: Jun. 25, 2018

(65) Prior Publication Data
US 2018/0369607 A1     Dec. 27, 2018

Related U.S. Application Data

(60) Provisional application No. 62/524,921, filed on Jun. 26, 2017.

(51) Int. Cl.
*A61B 5/00* (2006.01)
*A61N 5/06* (2006.01)
(Continued)

(52) U.S. Cl.
CPC ........ *A61N 5/0622* (2013.01); *A61B 5/04001* (2013.01); *A61B 5/0484* (2013.01);
(Continued)

(58) Field of Classification Search
CPC ................ A61N 5/0622; A61N 5/0601; A61N 1/37247; A61N 1/056; A61N 2005/0627;
(Continued)

(56) References Cited

U.S. PATENT DOCUMENTS 5,076,270 A    12/1991  Stutz, Jr.
5,437,193 A     8/1995  Schleitweiler et al.
(Continued)

FOREIGN PATENT DOCUMENTS

WO    2011150430    12/2011
WO    2012/103543    8/2012
WO    2014143387     9/2014

OTHER PUBLICATIONS

Vallejo, Ricardo, Kerry Bradley, and Leonardo Kapural. "Spinal cord stimulation in chronic pain: Mode of action." Spine 42 (2017): S53-S60.

(Continued)

*Primary Examiner* — Scott M. Getzow
(74) *Attorney, Agent, or Firm* — Lowe Graham Jones PLLC; Bruce E. Black

(57) ABSTRACT

An optical stimulation system includes a lead, a control module, and a control interface. The lead includes light emitters for emitting light having wavelengths that activate light-sensitive neurons. The light-sensitive neurons generate either an excitatory response or an inhibitory response when activated depending on the wavelength of the emitted light. The control module directs the emission of light from the light emitters using a set of stimulation parameters. The control interface includes user-selectable controls to adjust the stimulation parameters. The user-selectable controls include a graphical representation of a light emitter for each light emitter. Each graphical representation includes one or more user-selectable emitter controls to indicate whether a corresponding light emitter emits light and, if so, whether the emitted light generates an excitatory response or an inhibitory response from activated light-sensitive neurons.

20 Claims, 13 Drawing Sheets

(51) Int. Cl.
   *A61B 5/04* (2006.01)
   *A61B 5/0484* (2006.01)
   *A61B 17/00* (2006.01)
   *A61N 1/372* (2006.01)
   *A61N 1/05* (2006.01)

(52) U.S. Cl.
   CPC .......... *A61B 5/4836* (2013.01); *A61B 5/4839* (2013.01); *A61B 2017/00022* (2013.01); *A61B 2017/00199* (2013.01); *A61N 1/056* (2013.01); *A61N 1/37247* (2013.01); *A61N 5/0601* (2013.01); *A61N 2005/0612* (2013.01); *A61N 2005/0627* (2013.01); *A61N 2005/0652* (2013.01)

(58) Field of Classification Search
   CPC .... A61N 2005/0652; A61N 2005/0612; A61B 5/4836; A61B 5/04001; A61B 5/0484; A61B 2017/00022; A61B 5/4839; A61B 2017/00199
   See application file for complete search history.

(56) References Cited

U.S. PATENT DOCUMENTS

| | | |
|---|---|---|
| 5,445,608 A | 8/1995 | Chen et al. |
| 5,556,421 A | 9/1996 | Prutchi et al. |
| 6,175,710 B1 | 1/2001 | Kamaji et al. |
| 6,181,969 B1 | 1/2001 | Gord |
| 6,224,450 B1 | 5/2001 | Norton |
| 6,271,094 B1 | 8/2001 | Boyd et al. |
| 6,295,944 B1 | 10/2001 | Lovett |
| 6,364,278 B1 | 4/2002 | Lin et al. |
| 6,391,985 B1 | 5/2002 | Goode et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 6,988,001 B2 | 1/2006 | Greatbatch et al. |
| 6,993,384 B2 | 1/2006 | Bradley et al. |
| 7,190,993 B2 | 3/2007 | Sharma et al. |
| 7,244,150 B1 | 7/2007 | Brase et al. |
| 7,288,108 B2 | 10/2007 | DiMauro et al. |
| 7,395,118 B2 | 7/2008 | Erickson |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,684,869 B2 | 3/2010 | Bradley et al. |
| 7,736,382 B2 | 6/2010 | Webb et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,463,343 B2 | 6/2013 | Kuhn et al. |
| 8,473,061 B2 | 6/2013 | Moffitt et al. |
| 8,483,237 B2 | 7/2013 | Zimmermann et al. |
| 8,571,665 B2 | 10/2013 | Moffitt et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,831,742 B2 | 9/2014 | Pianca et al. |
| 8,849,632 B2 | 9/2014 | Sparks et al. |
| 8,936,630 B2 | 1/2015 | Denison et al. |
| 8,958,615 B2 | 2/2015 | Blum et al. |
| 9,415,154 B2 | 8/2016 | Leven |
| 9,550,063 B2 | 1/2017 | Wolf, II |
| 9,681,809 B2 | 6/2017 | Sharma et al. |
| 2002/0156513 A1 | 10/2002 | Borkan |
| 2002/0161417 A1 | 10/2002 | Scribner |
| 2005/0216072 A1 | 9/2005 | Mahadevan-Jansen et al. |
| 2006/0129210 A1 | 6/2006 | Cantin et al. |
| 2006/0155348 A1 | 7/2006 | deCharms |
| 2006/0161227 A1 | 7/2006 | Walsh, Jr. et al. |
| 2007/0053996 A1 | 3/2007 | Boyden et al. |
| 2007/0150036 A1 | 6/2007 | Anderson |
| 2007/0161919 A1 | 7/2007 | DiLorenzo |
| 2007/0203541 A1* | 8/2007 | Goetz ................ A61N 1/37247 607/59 |
| 2008/0046053 A1 | 2/2008 | Wagner et al. |
| 2008/0077198 A1 | 3/2008 | Webb et al. |
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2010/0076535 A1 | 3/2010 | Pianca et al. |
| 2010/0114190 A1 | 5/2010 | Bendett et al. |
| 2010/0174344 A1 | 7/2010 | Dadd et al. |
| 2010/0268298 A1 | 10/2010 | Moffitt et al. |
| 2010/0292758 A1 | 11/2010 | Lee et al. |
| 2010/0324630 A1 | 12/2010 | Lee et al. |
| 2011/0004267 A1 | 1/2011 | Meadows |
| 2011/0005069 A1 | 1/2011 | Pianca |
| 2011/0046432 A1 | 2/2011 | Simon et al. |
| 2011/0078900 A1 | 4/2011 | Pianca et al. |
| 2011/0125077 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172653 A1 | 7/2011 | Schneider et al. |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0253261 A1 | 10/2012 | Poletto et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0105071 A1 | 5/2013 | Digiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0304152 A1 | 11/2013 | Bradley et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067023 A1 | 3/2014 | Register et al. |
| 2014/0122379 A1 | 5/2014 | Moffitt et al. |
| 2014/0142664 A1 | 5/2014 | Roukes et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |

(56) References Cited

U.S. PATENT DOCUMENTS

| | | | |
|---|---|---|---|
| 2015/0066111 A1 | 3/2015 | Blum et al. | |
| 2015/0066120 A1 | 3/2015 | Govea | |
| 2015/0151113 A1 | 6/2015 | Govea et al. | |
| 2015/0306414 A1 | 10/2015 | Nielsen et al. | |
| 2015/0375006 A1* | 12/2015 | Denison | A61N 5/0622 607/88 |
| 2016/0030749 A1 | 2/2016 | Carcieri et al. | |
| 2016/0228692 A1 | 8/2016 | Steinke et al. | |
| 2016/0271392 A1 | 9/2016 | Vallejo et al. | |
| 2016/0346557 A1 | 12/2016 | Bokil | |
| 2016/0375258 A1 | 12/2016 | Steinke | |
| 2017/0061627 A1 | 3/2017 | Bokil | |
| 2017/0136254 A1 | 5/2017 | Simon et al. | |
| 2017/0225007 A1 | 8/2017 | Orinski | |
| 2017/0259078 A1 | 9/2017 | Howard | |
| 2017/0304633 A1 | 10/2017 | Zhang | |
| 2018/0064930 A1 | 3/2018 | Zhang et al. | |
| 2018/0078776 A1 | 3/2018 | Mustakos et al. | |
| 2018/0104482 A1 | 4/2018 | Bokil | |
| 2018/0110971 A1 | 4/2018 | Serrano Carmona | |
| 2018/0193655 A1 | 7/2018 | Zhang et al. | |
| 2018/0256906 A1 | 9/2018 | Pivonka et al. | |
| 2018/0369606 A1 | 12/2018 | Zhang et al. | |
| 2018/0369607 A1 | 12/2018 | Zhang et al. | |

OTHER PUBLICATIONS

Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

U.S. Appl. No. 16/242,370, filed Jan. 8, 2019, Zhang et al.
U.S. Appl. No. 16/242,461, filed Jan. 8, 2019, Hershey et al.
Baxter, G.D. et al., Effects of Low Intensity Infrared Laser Irradiation Upon Conduction in the Human Median Nerve In Vivo, Experimental Physiology (1994) 79, 227-234.
Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.
Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.
Snyder-Mackler, Lynn et al., Effect of Helium-Neon Laser Irradiation on Peripheral Sensory Nerve Latency, Phys. Ther. (1988), 68:223-225.
Darlot, Fannie et al., Near-infrared light is neuroprotective in a monkey model of Parkinson's disease (2006), 30 pages.
Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.
Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).
Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.
Use of NAD(P)H and flavoprotein autofluorescence transients to probe neuron and astrocyte responses to synaptic activation. Shuttleworth 2010 Neurochemestry international.
International Search Report and Written Opinion for PCT/US2018/039335 dated Oct. 12, 2018.

* cited by examiner

SYSTEMS AND METHODS FOR VISUALIZING AND CONTROLLING OPTOGENETIC STIMULATION USING OPTICAL STIMULATION SYSTEMS

CROSS-REFERENCE TO RELATED APPLICATIONS

This application claims the benefit under 35 U.S.C. § 119(e) of U.S. Provisional Patent Application Ser. No. 62/524,921, filed Jun. 26, 2017, which is incorporated herein by reference.

FIELD

The present invention is directed to the area of implantable optical stimulation systems and methods of making and using the systems. The present invention is also directed to systems and methods for visualizing and controlling optogenetic stimulation using optogenetic stimulation leads and systems, as well as methods of making and using the leads and optical stimulation systems.

BACKGROUND

Implantable optical stimulation systems can provide therapeutic benefits in a variety of diseases and disorders. For example, optical stimulation can be applied to the brain either externally or using an implanted stimulation lead to provide, for example, deep brain stimulation, to treat a variety of diseases or disorders. Optical stimulation may also be combined with electrical stimulation.

Stimulators have been developed to provide therapy for a variety of treatments. A stimulator can include a control module (for generating light or electrical signals sent to light sources in a lead), one or more leads, and one or more light sources coupled to, or disposed within, each lead. The lead is positioned near the nerves, muscles, or other tissue to be stimulated.

BRIEF SUMMARY

One embodiment is an optical stimulation system that includes an optical stimulation lead, a control module, and a control interface. The optical stimulation lead includes a lead body having a distal portion and a proximal portion, and light emitters disposed along the distal portion of the lead body. The light emitters are configured and arranged to emit light having wavelengths that activate light-sensitive neurons within a target stimulation location. The light-sensitive neurons generate either an excitatory response or an inhibitory response when activated, depending on the wavelength of the emitted light. The control module is coupleable to the optical stimulation lead and is configured and arranged to direct the emission of light from the light emitters using a set of stimulation parameters. The control interface is communicatively coupleable to the control module and includes user-selectable controls to adjust stimulation parameters of the set of stimulation parameters. The user-selectable controls include a graphical representation of a light emitter for each of the light emitters. Each graphical representation includes one or more user-selectable emitter controls to indicate whether that light emitter emits light and, if so, whether the emitted light includes a first wavelength that generates an excitatory response from activated light-sensitive neurons, or a second wavelength that generates an inhibitory response from activated light-sensitive neurons.

In at least some embodiments, the light emitter is configured and arranged to emit light having one or more wavelengths that activate light-sensitive neurons within a target stimulation location into which genetic agents were previously introduced.

In at least some embodiments, for each graphical representation the corresponding one or more user-selectable emitter controls enable the user to switch between selecting that the light emitter emits light that generates an excitatory response from activated light-sensitive neurons, and selecting that the light emitter emits light that generates an inhibitory response from activated light-sensitive neurons. In at least some embodiments, the control interface displays a graphical representation of the optical stimulation lead. In at least some embodiments, for each graphical representation, the graphical representation of the light emitter is disposed along the graphical representation of the optical stimulation lead.

In at least some embodiments, the control interface is configured and arranged to display a graphical representation of an activation volume based on user selection of the light emitters, the graphical representation of the activation volume depicting an estimated region where emitted light from the optical stimulation lead is sufficient to activate the light-sensitive neurons. In at least some embodiments, a size and shape of the graphical representation of the activation volume is based, at least in part, on at least one stimulation parameter of the set of stimulation parameters.

In at least some embodiments, the optical stimulation lead further includes a sensing electrode disposed along the distal portion of the lead body and coupleable to the control module, the sensing electrode configured and arranged to sense electrical activity from the light-sensitive neurons. In at least some embodiments, the sensing electrode is configured and arranged to sense electrical activity from the light-sensitive neurons during activation of the light-sensitive neurons. In at least some embodiments, the sensing electrode is configured and arranged to sense changes in electrical activity from the activated light-sensitive neurons in response to the emitted light. In at least some embodiments, for each of the graphical representations of activation volumes, the size and shape of that graphical representation of the activation volume is based, at least in part, on sensed electrical activity from the light-sensitive neurons received from the sensing electrode. In at least some embodiments, the control interface includes a user-selectable control for selecting which type of electrical activity from the light-sensitive neurons is sensed by the sensing electrode. In at least some embodiments, the sensing electrode is configured and arranged to sense at least one of a level of neuronal activation or neuronal firing rate of the light-sensitive neurons in response to the emitted light. In at least some embodiments, the sensing electrode is configured and arranged to sense at least one surrogate electrical signal from the light-sensitive neurons in response to the emitted light, the surrogate electrical signal usable for determining at least one of a level of neuronal activation or neuronal firing rate of the light-sensitive neurons in response to the emitted light. In at least some embodiments, the at least one surrogate electrical signal comprises one of an evoked compound action potential, a local field potential, a multiunit activity signal, an electroencephalogram signal, an electrophysiology signal, an electrospinogram signal, or an electroneurogram signal.

In at least some embodiments, the set of stimulation parameters includes at least one of intensity, pulse width, pulse frequency, cycling, or electrode stimulation configuration.

Another embodiment is a method for optically stimulating a patient. The method includes advancing the optical stimulation lead of the optical stimulation system described above in proximity to a target stimulation location within the patient, the target stimulation location containing light-sensitive neurons, the light-sensitive neurons generating either an excitatory response when activated by light of a first wavelength, or an excitatory response when activated by light of a second wavelength; selecting, for each light emitter, whether that light emitter emits light and, if so, whether the emitted light includes the first wavelength or the second wavelength; selecting at least one stimulation parameter of the set of stimulation parameters displayed by the control interface of the optical stimulation system; and emitting light towards the target stimulation location from each light emitter selected to emit light. In at least some embodiments, advancing the optical stimulation lead of the optical stimulation system described above in proximity to a target stimulation location within the patient includes advancing the optical stimulation lead in proximity to a target stimulation location into which genetic agents were previously introduced.

In at least some embodiments, selecting at least one stimulation parameter of the set of stimulation parameters includes selecting at least one of intensity, pulse width, pulse frequency, cycling, or electrode stimulation configuration. In at least some embodiments, selecting at least one stimulation parameter of the set of stimulation parameters includes selecting at least one stimulation parameter based, at least in part, on the size and shape of a graphical representation of an activation volume displayed on the control interface of the optical stimulation system. In at least some embodiments, selecting at least one stimulation parameter of the set of stimulation parameters includes selecting at least one stimulation parameter based, at least in part, on sensed electrical activity from the light-sensitive neurons. In at least some embodiments, selecting at least one stimulation parameter based, at least in part, on sensed electrical activity from the light-sensitive neurons includes selecting which type of electrical signals are sensed.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable optical stimulation systems and methods of making and using the systems. The present invention is also directed to systems and methods for visualizing and controlling optogenetic stimulation using optogenetic stimulation leads and systems, as well as methods of making and using the leads and optical stimulation systems.

In some embodiments, the implantable optical stimulation system only provides optical stimulation. Examples of optical stimulation systems with leads are found in, for example, U.S. patent application Ser. No. 15/450,969 which is incorporated by reference in its entirety. In other embodiments, the stimulation system can include both optical and electrical stimulation. In at least some of these embodiments, the optical stimulation system can be a modification of an electrical stimulation system to also provide optical stimulation. Suitable implantable electrical stimulation systems that can be modified to also provide optical stimulation include, but are not limited to, a least one lead with one or more electrodes disposed along a distal portion of the lead and one or more terminals disposed along the one or more proximal portions of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/

0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties.

Figure 1:
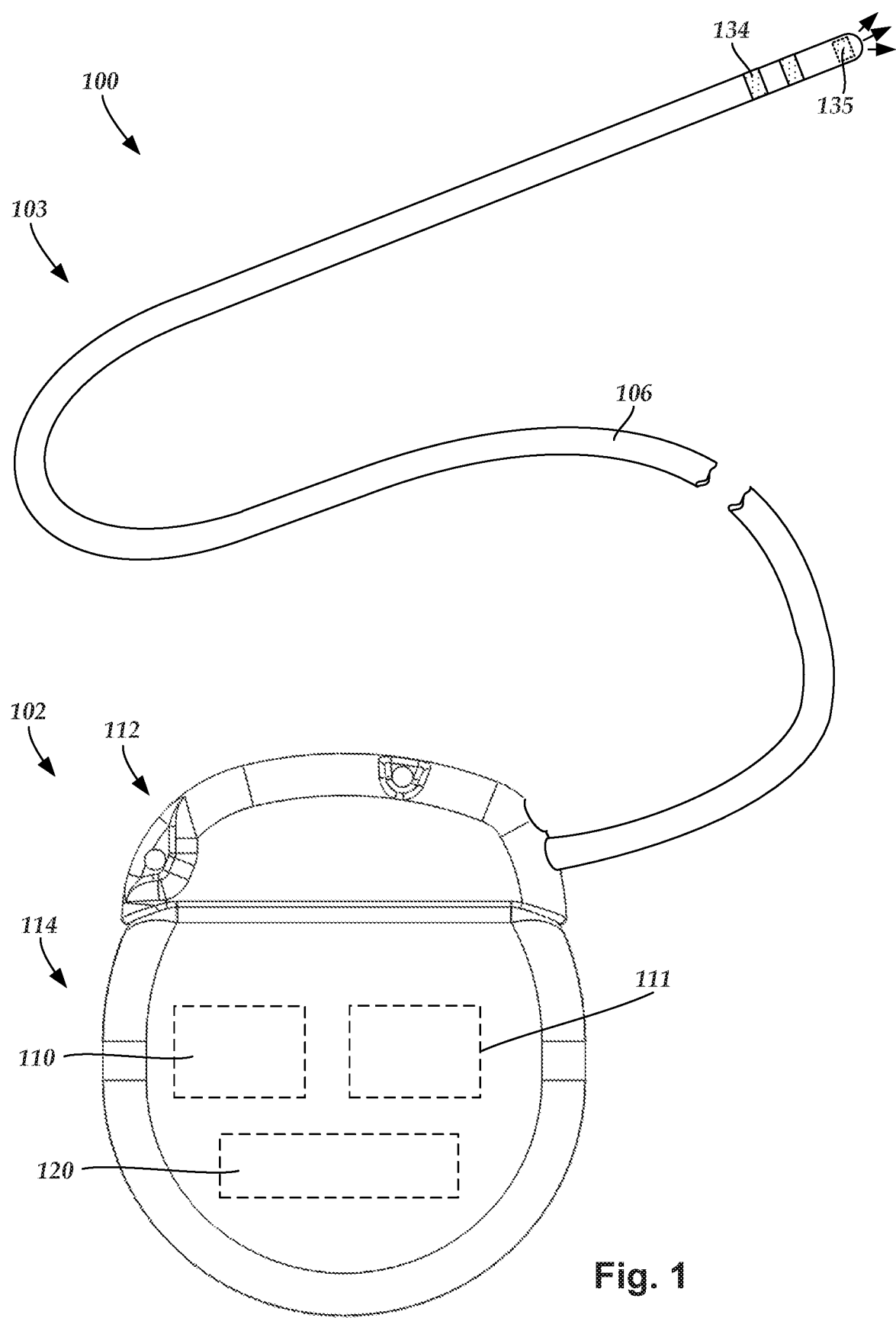
FIG. 1 is a schematic side view of one embodiment of an optical stimulation system that includes a lead coupled to a control module, according to the invention.
Figure 2A:
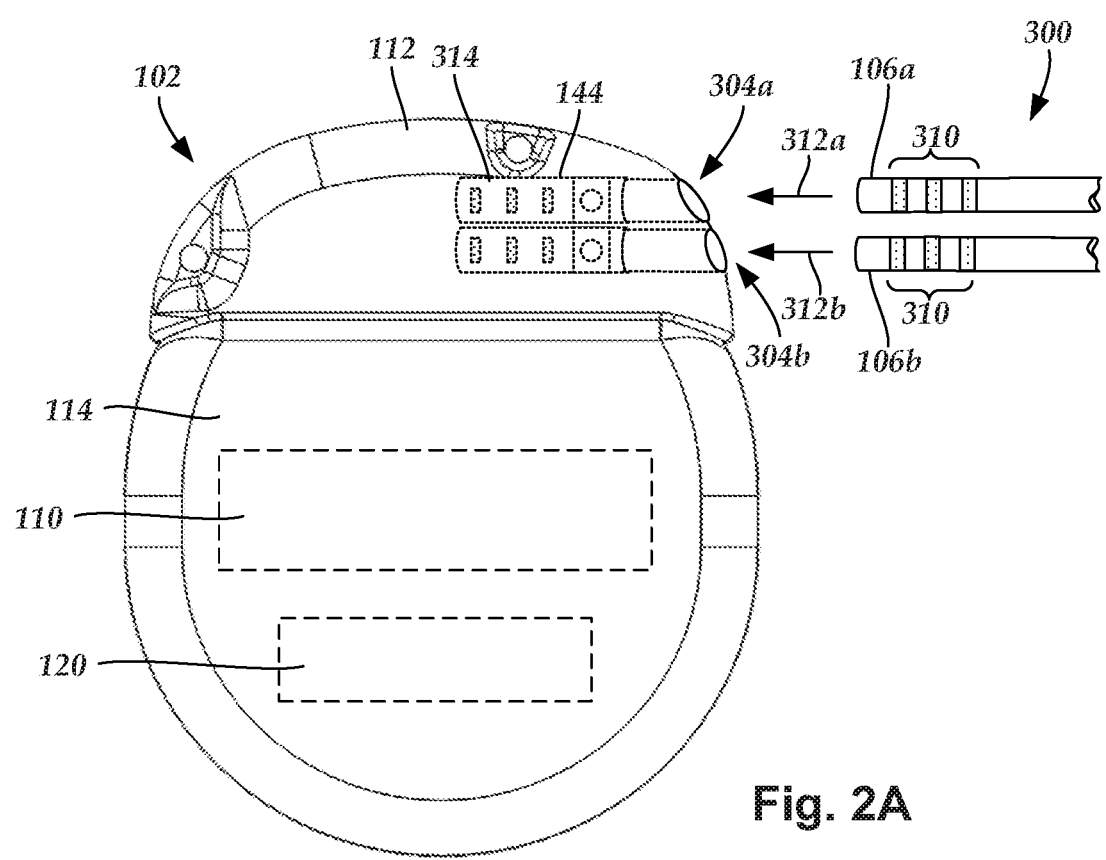
FIG. 2A is a schematic side view of one embodiment of the control module of FIG. 1 configured and arranged to couple to an elongated device, according to the invention.
Figure 2B:
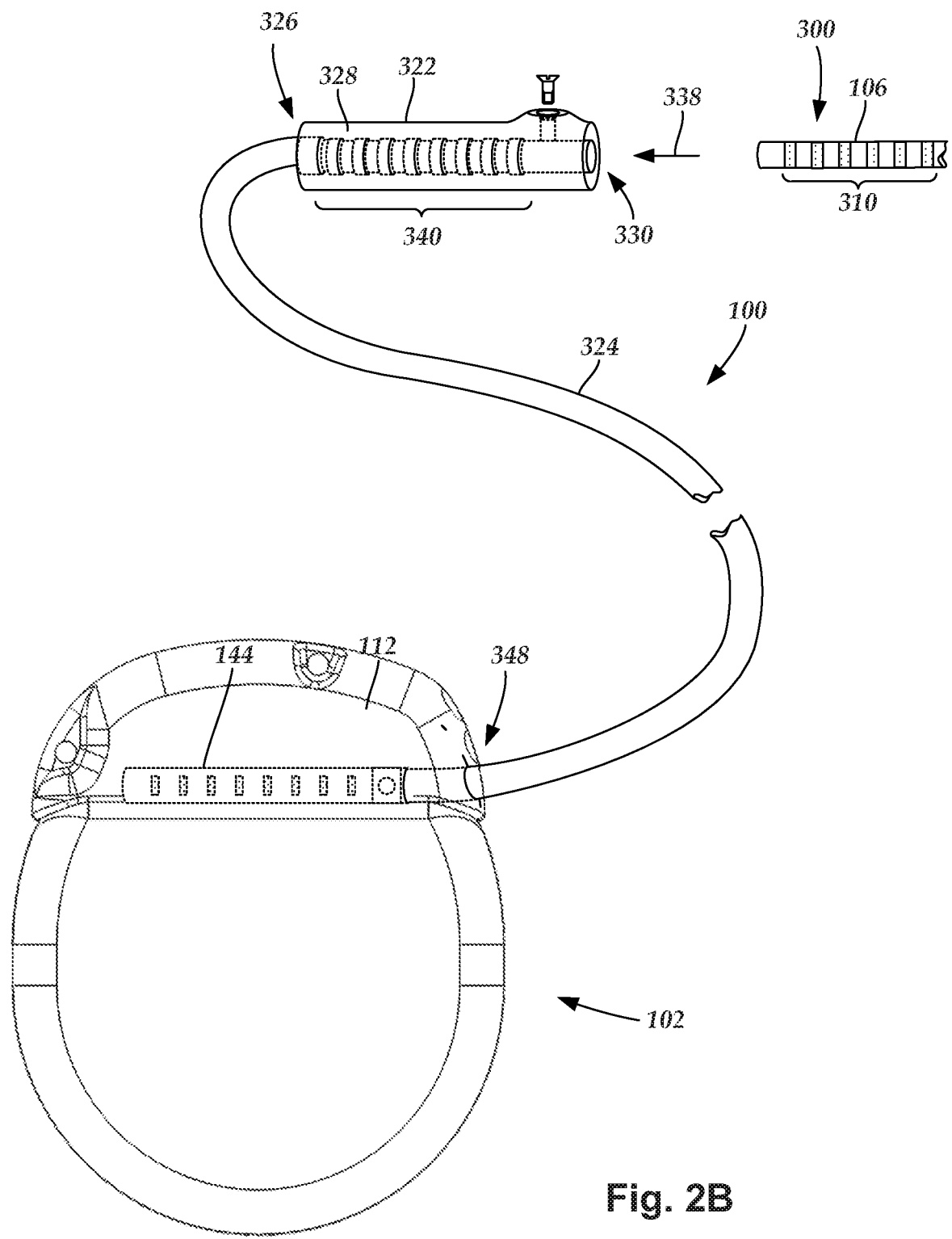
FIG. 2B is a schematic side view of one embodiment of a lead extension configured and arranged to couple the elongated device of FIG. 2A to the control module of FIG. 1, according to the invention.

FIG. 1 illustrates schematically one embodiment of an optical stimulation system 100. The optical stimulation system includes a control module (e.g., a stimulator) 102 and a lead 103 coupleable to the control module 102. The lead 103 includes one or more lead bodies 106. In FIG. 1, the lead 103 is shown having a single lead body 106. In FIG. 2B, the lead 103 includes two lead bodies. It will be understood that the lead 103 can include any suitable number of lead bodies including, for example, one, two, three, four, five, six, seven, eight or more lead bodies 106.

At least one light emitter 135 is provided along a distal portion of the lead 103. The light emitter 135 can be a light source, such as a light-emitting diode ("LED"), laser diode, organic light-emitting diode ("OLED"), or the like, or can be a terminus of a light transmission element, such as an optical fiber, in which case the light source is distant from the distal portion of the lead (for example, in the control module or in a proximal portion of the lead). The lead also includes electrodes 134 disposed along the lead body 106, and one or more terminals (e.g., 310 in FIG. 2A-2B) disposed along each of the one or more lead bodies 106 and coupled to the electrodes 134 by conductors (not shown). In at least some embodiments, one or more terminals (e.g., 310 in FIG. 2A-2B) may also be used to convey electrical signals to a light source that acts as the light emitter 135 by conductors (not shown) extending along the lead.

The electrodes 134 include at least one sensing electrode for sensing electrical activity. Optionally, the one or more electrodes 134 can include at least one stimulation electrode for providing electrical stimulation in addition to, or in lieu of, optical stimulation provided via the at least one light emitter 135.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. In at least some embodiments, at least one of the electrodes 134 is formed from an optically-transparent material. Any suitable number of electrodes 134 can be disposed on the lead including, for example, one, two, three, four, five, six, seven, eight, nine, ten, eleven, twelve, fourteen, sixteen, twenty-four, thirty-two, or more electrodes 134.

The lead 103 can be coupled to the control module 102 in any suitable manner. In some embodiments, the lead is permanently attached to the control module 102. In other embodiments, the lead can be coupled to the control module 102 by a connector (e.g., connector 144 of FIG. 2A). In FIG. 2A, the lead 103 is shown coupling directly to the control module 102 through the connector 144. In at least some other embodiments, the lead 103 couples to the control module 102 via one or more intermediate devices, as illustrated in FIG. 2B. For example, in at least some embodiments one or more lead extensions 324 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the stimulation system 100 includes multiple elongated devices disposed between the lead 103 and the control module 102, the intermediate devices may be configured into any suitable arrangement.

The control module 102 can include, for example, a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

In some embodiments, the control module 102 also includes one or more light sources 111 disposed within the sealed electronics housing 114. In alternate embodiments, the one or more light sources 111 are external to the control module. The one or more light sources can be, for example, a light-emitting diode ("LED"), laser diode, organic light-emitting diode ("OLED"), or the like. When the control module 102 includes multiple light sources, the light sources can provide light in at a same wavelength or wavelength band or some, or all, of the light sources can provide light at different wavelength or different wavelength bands. When the one or more light sources 111 are external to the lead(s), the light emitted by the light sources can be directed to one or more optical fibers (for example, optical fibers 420a, 420b in FIG. 4) or other light-transmitting body. The optical fiber, or a series of optical fibers, can transmit the light from the one or more light sources 111 through the control module 102 and lead 103 to the light emitter 135 (which can be terminus of the optical fiber). In at least some embodiments, the optical fiber is a single mode optical fiber. In other embodiments, the optical fiber is a multi-mode optical fiber. In some embodiments, the system includes a single optical fiber. In other embodiments, the system may employ multiple optical fibers in series or in parallel.

In other embodiments, the light emitter 135 can also be the light source (a light-emitting diode ("LED"), laser diode, organic light-emitting diode ("OLED"), or the like), or a combination of light sources, with conductors extending along the lead 103 and coupled to the electronic subassembly 110 to provide signals and power for operating the light source. In yet other embodiments, the light source can be disposed elsewhere in the control module 102, on the lead 103, in another element such as a lead extension, splitter, adaptor, or other stand-alone element.

The stimulation system or components of the stimulation system, including the lead 103 and the control module 102, are typically implanted into the body of a patient. The stimulation system can be used for a variety of applications including, but not limited to brain stimulation, deep brain stimulation, neural stimulation, spinal cord stimulation, muscle stimulation, sacral nerve stimulation, dorsal root ganglion stimulation, peripheral nerve stimulation, and the like.

The one or more lead bodies 106 are made of a non-conductive, biocompatible material such as, for example, silicone, polyurethane, polyether ether ketone ("PEEK"), epoxy, and the like or combinations thereof. The one or more lead bodies 106 may be formed in the desired shape by any process including, for example, molding (including injection molding), casting, and the like.

One or more terminals (e.g., 310 in FIGS. 2A-2B) are typically disposed along the proximal end of the one or more lead bodies 106 of the stimulation system 100 (as well as any splitters, lead extensions, adaptors, or the like) for electrical connection to corresponding connector contacts (e.g., 314 in FIGS. 2A-2B). The connector contacts are disposed in connectors (e.g., 144 in FIGS. 1-2B; and 322 FIG. 2B) which, in turn, are disposed on, for example, the control module 102 (or a lead extension, a splitter, an adaptor, or the like). Electrically conductive wires, cables, or the like (not shown) extend from the terminals to the light emitter 135 or electrodes 134.

The electrically-conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal portion of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 2B, an adaptor, or the like or combinations thereof), or a combination thereof.

The control module connector 144 defines at least one port into which a proximal end of the elongated device 300 can be inserted, as shown by directional arrows 312a and 312b. In FIG. 2A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Each of the terminals 310 can couple to the light emitter 135 or one or more of the electrodes 134. Examples of connectors in control modules are found in, for example, U.S. Pat. Nos. 7,244,150 and 8,224,450, which are incorporated by reference.

FIG. 2B is a schematic side view of another embodiment of the stimulation system 100. The stimulation system 100 includes a lead extension 324 that is configured and arranged to couple one or more elongated devices 300 (e.g., one of the lead bodies 106 of FIG. 1, a splitter, an adaptor, another lead extension, or the like or combinations thereof) to the control module 102. In FIG. 2B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144 (e.g., the ports 304a and 304b of FIG. 1), or to receive multiple elongated devices 300 (e.g., both of the lead bodies 106 of FIG. 1), or both.

A lead extension connector 322 is disposed on the lead extension 324. In FIG. 2B, the lead extension connector 322 is shown disposed at a distal portion 326 of the lead extension 324. The lead extension connector 322 includes a connector housing 328. The connector housing 328 defines at least one port 330 into which terminals 310 of the elongated device 300 can be inserted, as shown by directional arrow 338. Each of the terminals 310 can couple to the light emitter 135 or one or more of the electrodes 134. The connector housing 328 also includes a plurality of connector contacts, such as connector contact 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIG. 1) disposed along the lead (103 in FIG. 1).

In at least some embodiments, the proximal end of the lead extension 324 is similarly configured and arranged as a proximal end of the lead 103 (or other elongated device 300). The lead extension 324 may include a plurality of electrically-conductive wires (not shown) that electrically couple the connector contacts 340 to a proximal portion 348 of the lead extension 324 that is opposite to the distal portion 326. In at least some embodiments, the conductive wires disposed in the lead extension 324 can be electrically coupled to a plurality of terminals (not shown) disposed along the proximal portion 348 of the lead extension 324. In at least some embodiments, the proximal portion 348 of the lead extension 324 is configured and arranged for insertion into a connector disposed in another lead extension (or another intermediate device). In other embodiments (and as shown in FIG. 2B), the proximal portion 348 of the lead extension 324 is configured and arranged for insertion into the control module connector 144.

Figure 3:
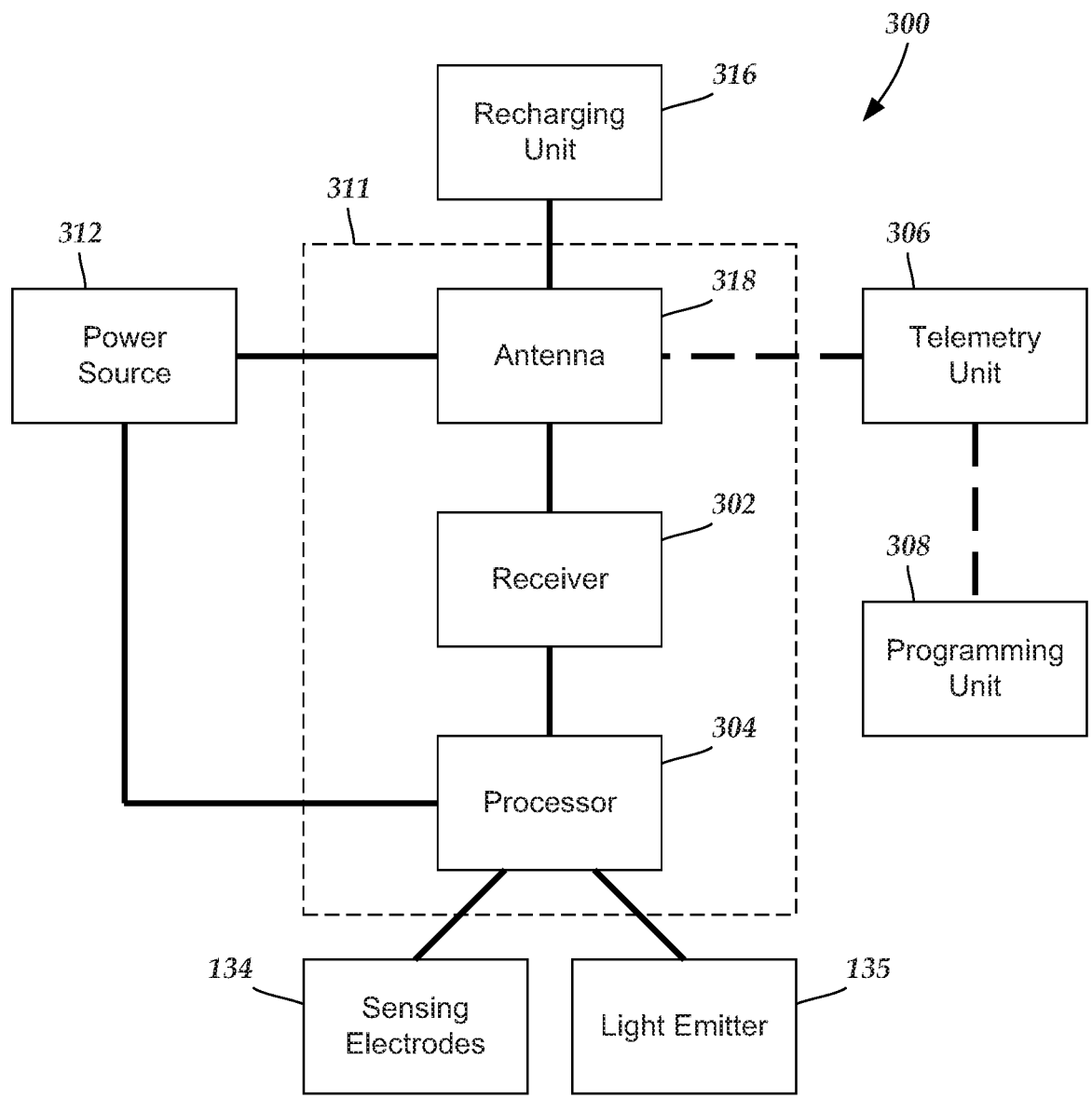
FIG. 3 is a schematic overview of one embodiment of components of a stimulation system, including an electronic subassembly disposed within a control module, according to the invention.

FIG. 3 is a schematic overview of one embodiment of components of an optical stimulation system 300 including an electronic subassembly 311 disposed within a control module. It will be understood that the optical stimulation system can include more, fewer, or different components and can have a variety of different configurations including those configurations disclosed in the stimulator references cited herein.

Some of the components (for example, a power source 312, an antenna 318, a receiver 302, and a processor 304) of the optical stimulation system can be positioned on one or more circuit boards or similar carriers within a sealed housing of an implantable pulse generator, if desired. Any power source 312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 318 or a secondary antenna. The external power source can be in a device that is mounted on the skin of the user or in a unit that is provided near the user on a permanent or periodic basis.

If the power source 312 is a rechargeable battery, the battery may be recharged using the optional antenna 318, if desired. Power can be provided to the battery for recharging by inductively coupling the battery through the antenna to a recharging unit 316 external to the user. Examples of such arrangements can be found in the references identified above.

In one embodiment, light is emitted by the light emitter 135 of the lead body to stimulate nerve fibers, muscle fibers, or other body tissues near the optical stimulation system. The processor 304 is generally included to control the timing and other characteristics of the optical stimulation system. For example, the processor 304 can, if desired, control one or more of the intensity, wavelength, amplitude, pulse width, pulse frequency, cycling (e.g., for repeating intervals of time, determining how long to stimulate and how long to not stimulate), and electrode stimulation configuration (e.g., determining electrode polarity and fractionalization) of the optical stimulation.

Additionally, the processor 304 can select which, if not all, of the sensing electrodes are activated. Moreover, the processor 394 can control which types of signals the sensing electrodes detect. In at least some embodiments, the sensing electrodes detect a level of neuronal activation, or neuronal firing rates, or both, received directly from the target stimulation location. In other embodiments, the sensing electrodes detect one or more other signals received from the target stimulation location in addition to, or in lieu of the level of neuronal activation or neuronal firing rates, such as evoked compound action potentials, local field potentials, multiunit activity, electroencephalograms, electrophysiology, or electroneurograms. In at least some embodiments, one or more of the received signals (e.g., evoked compound action potentials, local field potentials, multiunit activity, electroencephalograms, electrophysiology, electroneurograms, or the like) can be used to indirectly measure the level of neuronal activation, or neuronal firing rates, or both, at the target stimulation location.

Optionally, the processor 304 can select one or more stimulation electrodes to provide electrical stimulation, if desired. In some embodiments, the processor 304 selects which of the optional stimulation electrode(s) are cathodes and which electrode(s) are anodes.

Any processor can be used and can be as simple as an electronic device that, for example, produces optical stimulation at a regular interval or the processor can be capable of receiving and interpreting instructions from an external programming unit 308 that, for example, allows modification of stimulation characteristics. In the illustrated embodiment, the processor 304 is coupled to a receiver 302 which, in turn, is coupled to the optional antenna 318. This allows the processor 304 to receive instructions from an external source to, for example, direct the stimulation characteristics and the selection of electrodes, if desired.

In one embodiment, the antenna 318 is capable of receiving signals (e.g., RF signals) from an external telemetry unit 306 which is programmed by the programming unit 308. The programming unit 308 can be external to, or part of, the telemetry unit 306. The telemetry unit 306 can be a device that is worn on the skin of the user or can be carried by the user and can have a form similar to a pager, cellular phone, or remote control, if desired. As another alternative, the telemetry unit 306 may not be worn or carried by the user but may only be available at a home station or at a clinician's office. The programming unit 308 can be any unit that can provide information to the telemetry unit 306 for transmission to the optical stimulation system 300. The programming unit 308 can be part of the telemetry unit 306 or can provide signals or information to the telemetry unit 306 via a wireless or wired connection. One example of a suitable programming unit is a computer operated by the user or clinician to send signals to the telemetry unit 306.

The signals sent to the processor 304 via the antenna 318 and the receiver 302 can be used to modify or otherwise direct the operation of the optical stimulation system. For example, the signals may be used to modify the stimulation characteristics of the optical stimulation system such as modifying one or more of stimulation duration, pulse frequency, waveform, and stimulation amplitude. The signals may also direct the optical stimulation system 300 to cease operation, to start operation, to start charging the battery, or to stop charging the battery. In other embodiments, the stimulation system does not include the antenna 318 or receiver 302 and the processor 304 operates as programmed.

Optionally, the optical stimulation system 300 may include a transmitter (not shown) coupled to the processor 304 and the antenna 318 for transmitting signals back to the telemetry unit 306 or another unit capable of receiving the signals. For example, the optical stimulation system 300 may transmit signals indicating whether the optical stimulation system 300 is operating properly or not or indicating when the battery needs to be charged or the level of charge remaining in the battery. The processor 304 may also be capable of transmitting information about the stimulation characteristics so that a user or clinician can determine or verify the characteristics.

Figure 4:
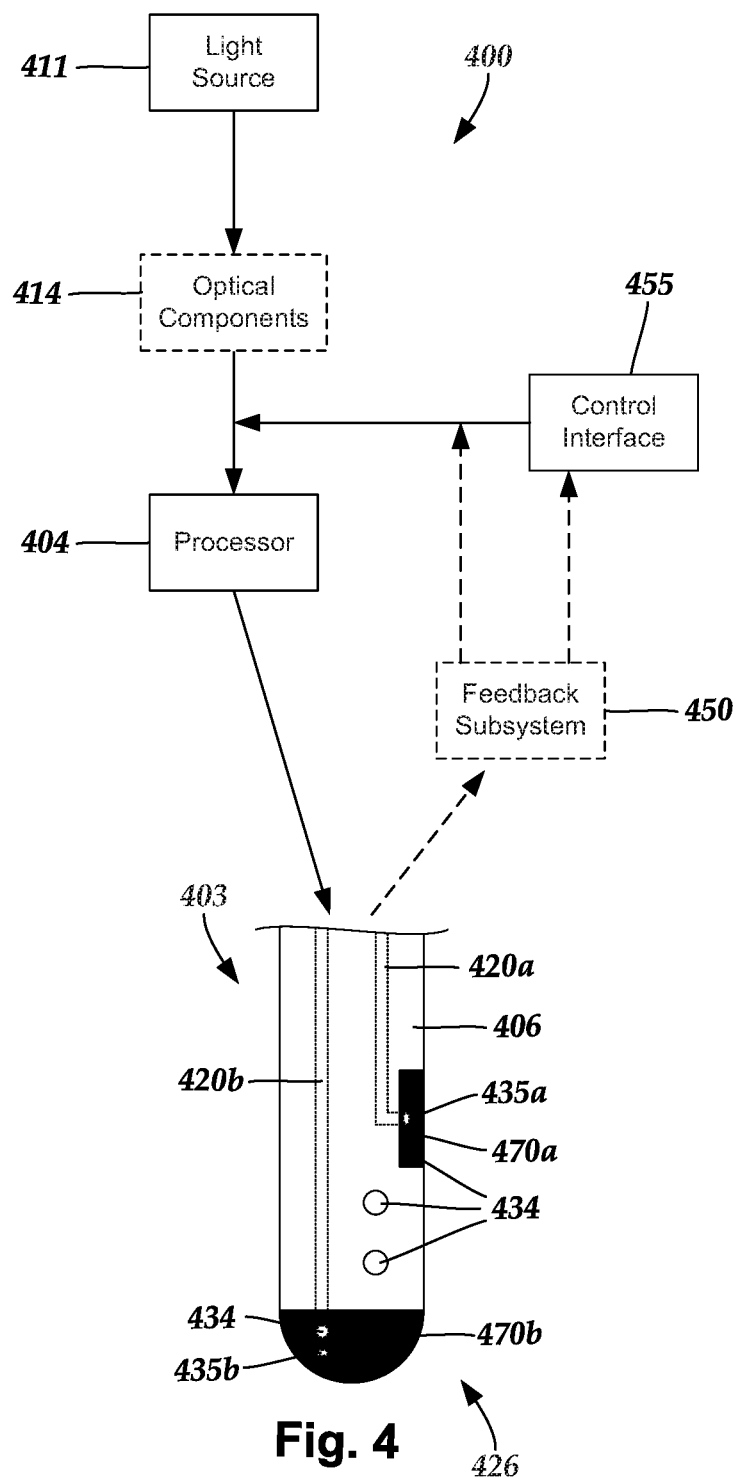
FIG. 4 is a schematic overview of one embodiment of an optical stimulation lead with a light source, a processor, and a control interface, according to the invention.

Turning to FIG. 4, optogenetics is a type of optical stimulation that uses light to control, measure, or monitor activities of neurons into which one or more genetic agents have been introduced. The introduced genetic agents cause a measurable effect in the neurons (e.g., excitation, inhibition) when optically stimulated at certain wavelengths. Cells that have not received the genetic agent typically do not elicit a similar effect from the optical stimulation as cells that receive the genetic agents. In some instances, cells that have not received the genetic agent may elicit a smaller (e.g., subthreshold) effect from the optical stimulation than cells that receive the genetic agents.

Any suitable technique can be used for introducing the genetic agent(s) to cells at a target stimulation location including, for example, transduction, transfection, or both. In at least some embodiments, the genetic agents are introduced into cells using viral vectors. Delivery of the genetic agent(s) can be intravenously, intracranially, or the like or combinations thereof. Optogenetics can be used to provide therapy for a variety of different disorders or conditions including, for example, chronic pain, spinal cord injury sensory function (e.g., transfecting sensory neurons to reactivate them), spinal cord injury motor function (e.g., transfecting sensory neurons to reactivate them), chronic itch, inflammatory pain (e.g., arthritis), pain associated with cancer, overactive bladder, incontinence, sexual dysfunction following spinal cord injury/neuropathy, diabetic neuropathy/peripheral neuropathy, multiple sclerosis, and other disorders or conditions that might have a peripheral/spinal etiology which could be modulated by controlling the activity of spinal sensory or motor neurons.

Optogenetics may provide advantages over electrical stimulation. Optogenetics may provide increased specificity of stimulation, as compared to electrical stimulation. For example, a light emitter may be much smaller in size than an implanted electrical stimulation electrode. Optical stimulation specificity may be further affected by other factors, such as absorbance of light, the amount/uptake of introduced genetic agents, inhibition in and around the target optical stimulation location. Accordingly, the region of tissue stimulated by optical stimulation may be much smaller in size than a region of tissue stimulated by electrical stimulation. Increased specificity of stimulation at a target location may potentially reduce undesired side effects caused by collateral stimulation of untargeted patient tissue.

Additionally, optogenetics can enable concurrent sensing/recording of electrical activity (e.g., neural activity, such as a level of neuronal activation or neuronal firing rates) during stimulation. In contrast, electrical stimulation may mask base-line electrical activity because the current needed to depolarize cells at a target stimulation location may obscure the base-line electrical activity within (or in proximity to) the target stimulation location.

Light-sensitive neurons have at least one channel, tertiary protein structure, etc. that undergoes a distinct conformal, physiological, electrophysiological, and/or electrical change of at least a portion of the neuron in response to one or more specific wavelengths of light. Genetic agent(s) introduced into the cells can encode for one or more light-sensitive proteins, such as opsins, related to the production of ion channels. The encoded light-sensitive proteins are activated (e.g. stimulated to open or close a channel, drive a pump to raise or lower the membrane potential of a cell, or the like) within a particular range of wavelengths.

Suitable light-sensitive proteins include, for example, channelrhodopsins, halorhodopsins, archaerhodopsins, or other ion-channel-related proteins. The particular wavelength ranges over which the encoded proteins are activated may be different for different proteins. In at least some embodiments, channelrhodopsin is responsive in the range of 425 nm-475 nm, while halorhodopsin is responsive in range of 550 nm-600 nm. The activation wavelength ranges for different genetic agents may, or may not, overlap with one another.

Suitable target stimulation locations include, but are not limited to, at least one of the patient's brain, spinal cord, cauda equina, one or more dorsal root entry zones, one or more dendritic cells, one or more dorsal root ganglia, or one or more spinothalamic tracts, peripheral sensory and motor nerves, peripheral plexi (e.g. brachial, solar, mesenteric, and the like), peripheral receptors, free nerve endings, rootlets, distal axons of dorsal root ganglia (peripheral nerves), dorsal columns.

In at least some embodiments, genetic agents are delivered to multiple target stimulation locations (e.g., dorsal root ganglion and dendritic cells) from the same location either concurrently or sequentially.

The optical stimulation lead can be positioned in proximity to the target stimulation location(s) before, during, or after introduction of the genetic agent(s) into cells of the target stimulation location. In some embodiments, one or more excitatory genetic agents are exclusively delivered to cells. In other embodiments, one or more inhibitory genetic agents are exclusively delivered to cells. In at least some embodiments, multiple types of genetic agents are delivered to cells. In some instances, the delivered genetic agents include at least one type of excitatory genetic agent and at least one type of inhibitory genetic agent, where the excitatory genetic agent and the inhibitory genetic agent are activated at different wavelengths, or ranges of wavelengths. In at least some embodiments, an excitatory agent and an inhibitory agent are delivered into cells together. For example, an excitatory agent and an inhibitory agent can be part of the same viral vector.

At some point after expression of the genetic agents begins within the cells at the target stimulation location, light is emitted by the optical stimulation lead towards the target stimulation location from a position in proximity to the target stimulation location. Light is emitted via the one or more light emitters. In at least some embodiments, one or more electrical signals output from neurons within the target stimulation location are sensed by one or more sensing electrodes.

FIG. 4 schematically shows one embodiment of an optical lead system 400 that includes a lead 403 with a lead body 406. Optical fibers 420a, 420b disposed in the lead 403 couple light emitters 435a, 435b, respectively, disposed along a distal portion 426 of the lead 403 to a light source 411 (for generating light) and a processor 404 (for applying one or more stimulation parameters to the generated light, turning off one or more of the light emitters, or the like). The light emitters 435a, 435b may, optionally, be disposed beneath optically-transparent regions 470a, 470b, respectively, through which light emitted from the light emitters passes. Optional sensing electrodes 434 are disposed along the distal portion 426 of the lead and are also coupled to the processor 404 via one or more electrical conductors (not shown).

The light source 411 generates the light emitted by the light emitters 435a, 435b. Optionally, the light is passed through one or more optical components 414 (e.g., collimators, optical lenses, optical filters, or the like) to alter characteristics of the light prior to emission from the light emitters 435a, 435b. In the illustrated embodiment, the optical components 414 are shown positioned between the light source 411 and the processor 404. It will be understood that the one or more optical components 414 can, alternatively or additionally, be disposed between the processor 404 and the lead 403, along the exterior of the lead body 406, embedded within the lead body, or any combination thereof.

The light generated by the light source can be within any suitable range of wavelengths for providing optical therapy, including infrared, visible, or ultraviolet wavelengths. In at least some embodiments, the light is emitted in one or more narrow bands of wavelengths (e.g., a band having a range of no more than 100 nm, 50 nm, 25 nm, 20 nm, 15 nm, 10 nm, or 5 nm). In at least some embodiments, the wavelengths are no less than 400 nm. In at least some embodiments, the wavelengths are no greater than 650 nm. In at least some embodiments, the wavelengths are no less than 425 nm and no greater than 600 nm. In at least some embodiment, the wavelengths are no less than 425 nm and no greater than 475 nm. In at least some embodiment, the wavelengths are no less than 550 nm and no greater than 600 nm.

The illustrated embodiment shows two optical fibers 420a, 420b. Any suitable number of optical fibers may be utilized including, one, two, three, four, five, six, seven, eight, nine, ten, eleven, twelve, fourteen, sixteen, eighteen, twenty, thirty, or more optical fibers. In at least some embodiments, there is an optical fiber for every light emitter.

As an alternative to the optical fibers, one or more light emitting diodes (LEDs), organic light emitting diodes (OLEDs), laser diodes, or other light sources may be disposed along the distal portion of the lead to provide the light. For example, one or more white light sources can be disposed along the distal portion of the lead. Alternatively, one or more light sources for each of multiple colors, wavelengths, or wavelength bands can be disposed along the distal portion of the lead. These light sources can be electrically coupled to the control module by conductors that extend along the lead. The control module can then direct turning on and off the light sources, leads (if multiple leads are implanted), as well as other stimulation parameters such as intensity, wavelength, amplitude, pulse width, pulse frequency, cycling, electrode stimulation configuration, and the like using signals sent to the light source(s) over the conductors.

Light is emitted to the target stimulation location(s) via the one or more light emitters. In the illustrated embodiment, the light emitter 435a is disposed along a side of the lead and is side-facing (i.e., light is emitted outwardly from a side of the lead), and the light emitter 435b is disposed at a distal tip of the lead and is forward-facing (i.e., light is emitted distally outwardly from the distal tip of the lead). Alternatively, all of the light emitters can be side-facing, or all of the light emitters can be forward-facing. In at least some embodiments, therapy is directed towards two or more target stimulation locations that are stimulated concurrently or sequentially from the same lead position. In which case, one or more of the light emitters can be directed to one of the target stimulation locations, while one or more of the remaining light emitters are directed to a different target stimulation location. In at least some embodiments, multiple light emitters are directed towards the same target stimulation location.

As mentioned above, some genetic agents delivered to cells cause an excitatory response, while others cause an inhibitory response. The wavelengths at which the particular genetic agents are activated may be different. Thus, a first stimulation wavelength may activate a first genetic agent that generates an excitatory response, while a second stimulation wavelength that is different than the first stimulation wavelength may activate a second genetic agent that generates an inhibitory response.

Accordingly, activation by optical stimulation can cause neurons to become excited or become inhibited, depending on which type of genetic agent is introduced into those neurons, and which wavelengths of light are used to stimulate those neurons. In some instances, both excitatory and inhibitory genetic agents are introduced into the same neurons. In which case, selectively switching between an excitatory range of wavelengths and an inhibitory range of wavelengths (i.e., steering) can be used to elicit either an excitatory response or an inhibitory response from those neurons.

Figure 5:
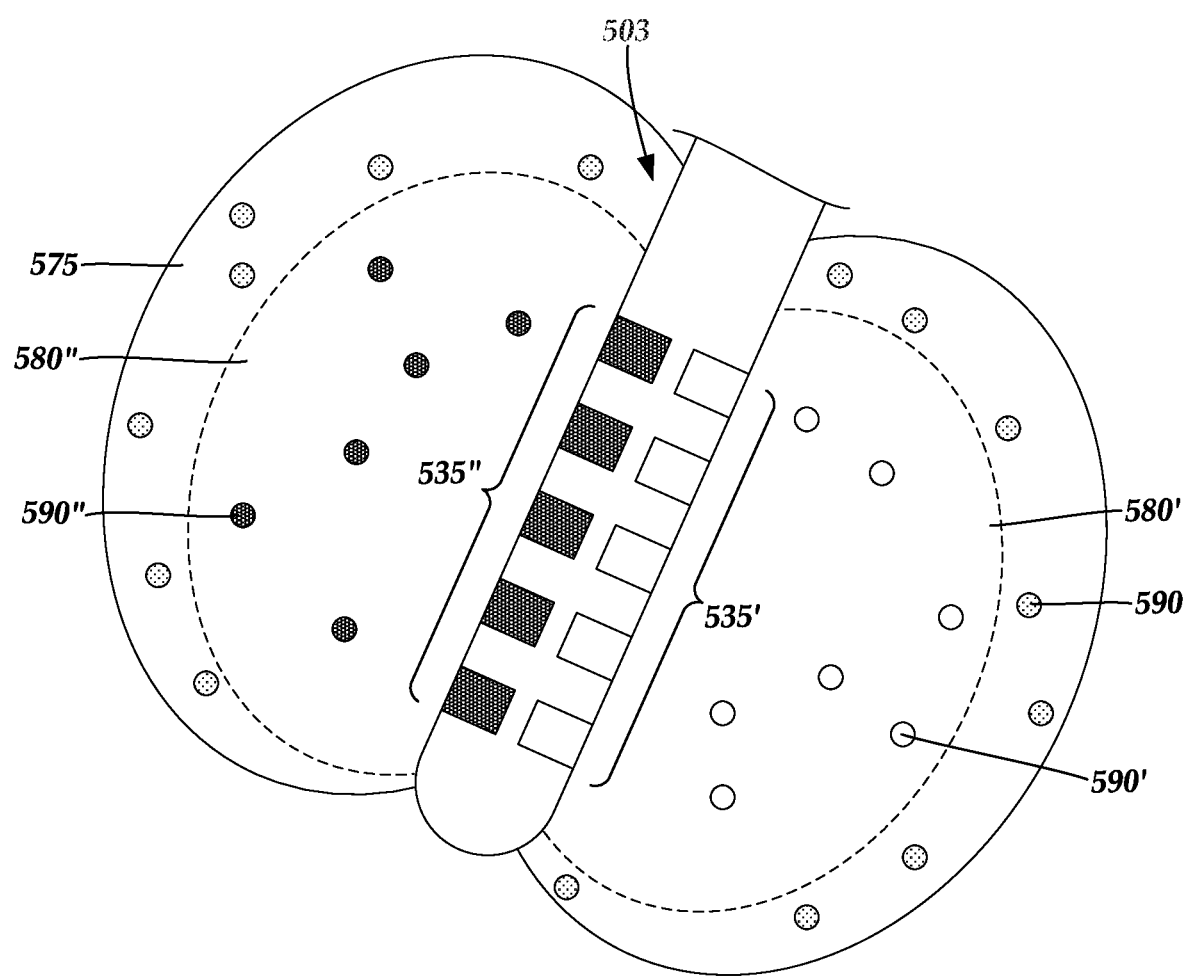
FIG. 5 is a schematic side view of one embodiment of a distal portion of an optical stimulation lead and an activation field generated by light emitters of the optical stimulation lead, according to the invention.

FIG. 5 shows one embodiment of a distal portion of a lead 503 disposed within a target stimulation location 575. Multiple neurons (indicated as lightly-stippled circles), such as neuron 590, are disposed in the target stimulation location 575. Both excitatory and inhibitory genetic agents have been introduced into the neurons within the target stimulation location 575, such that neurons can either be inhibited by light emitted at a first activation wavelength or excited by light emitted at a second activation wavelength.

Light emitters are disposed along opposing sides of the lead. In FIG. 5, and in other figures, light emitters configured for emitting light at an inhibitory activation wavelength, such as light emitters 535' in FIG. 5, are shown in solid white and are hereinafter referred to as "inhibiting emitters", while light emitters configured for emitting light at an excitatory activation wavelength, such as light emitters 535" in FIG. 5, are shown as heavily stippled and are hereinafter referred to as "exciting emitters". In some embodiments, the light emitters can be individually programmed to emit light at either the first wavelength or the second wavelength. In some embodiments, the light emitters can also be individually programmed to turn off. Individually adjusting the light emitters to be inhibiting, exciting, or off, can potentially change the sizes, shapes, and locations of the activation volumes.

In the illustrated embodiment, a first activation volume 580' is shown extending generally outwards from the inhibiting emitters 535' in response to light emitted at the first activation wavelength. Neurons 590' within the first activation volume 580' are inhibited, as indicated by no stippling, while neurons that are inside the target stimulation location 575 yet outside of the first activation volume 508', are not inhibited. A second activation volume 580" is shown extending generally outwards from the exciting emitters 535" in response to light emitted at the second activation wavelength. Neurons 590" within the second activation volume 580" are excited, as indicated by heavy stippling, while neurons that are inside the target stimulation location 575 yet outside of the second activation volume 580", are not excited.

Turning back to FIG. 4, the sizes and shapes of the activation volumes are influenced by the stimulation parameters of the emitted light. The sizes and shapes obtained using a given set of stimulation parameters can, optionally, be sensed using sensing electrodes. The one or more sensing electrodes 434 are disposed along the distal Turning back to FIG. 4, the sizes and shapes of the activation volumes are influenced by the stimulation parameters of the emitted light. The sizes and shapes obtained using a given set of stimulation parameters are sensed using sensing electrodes. The one or more sensing electrodes 434 are disposed along the distal portion of the lead and adapted to sense one or more electric signals. The electric signals can include background signals, signals emitted in response to optical stimulation, or both. The one or more sensed electrical signals can include sensing changes in electrical activity in at least some cells within the target stimulation location in response to the optical stimulation. The sensing electrodes can be adapted to sense various different types of signals from targeted cell populations including, for example, one or more of sensing a level of neuronal activation, or neuronal firing rates, or both.

Signals from targeted cell populations can be sensed directly, or indirectly (i.e., a surrogate) using any electrical signal recordable from the nervous system that indicates neural activity. Suitable surrogate signals include, for example, evoked compound action potentials, local field potentials, multiunit activity signals (e.g., determining neuronal firing rates by counting spikes per unit of time), electroneurogram signals (e.g., measuring activity in peripheral nerves based on a response-to-noise ratio), electroencephalogram signals, electrophysiology signals, or the like or combinations thereof received from the target stimulation location. In at least some embodiments, the changes in the sensed signals correspond to one or more disorders or conditions of interest.

As shown in FIG. 4, an optional closed-loop feedback subsystem 450 couples the processor 404 to the sensing electrodes 434. Electrical signals sensed from the sensing electrodes may provide information about the sizes and shapes of the activation volumes which, in turn, can be used to adjustment stimulation to improve therapy. Accordingly, the closed-loop feedback subsystem 450 can be used to adjust one or more parameters of the emitted light (e.g., intensity, wavelength, amplitude, pulse width, pulse frequency, cycling, electrode stimulation configuration, and the like) based on the sensed electrical signals (e.g., sensing of a new signal, sensing a change in the amount or quality of a signal, the disappearance of a signal, or the like).

The one or more sensing electrodes can be disposed at any location suitable for sensing and recording electrical activity from cells at the target stimulation location. The sensing electrodes can be disposed along the lead body. In some embodiments, the sensing electrodes are disposed along one or more optically-transparent regions of the lead body. In some instances, one or more of the sensing electrodes are disposed on, or in proximity to, one or more of the light emitters. In some instances, one or more of the sensing electrodes are disposed on, or in proximity to, one or more of the optical fibers.

In the embodiment illustrated in FIG. 4, sensing electrodes 434 are shown disposed in the lead body 406, and also on the optical fiber 420*b* in proximity to the forward-facing light emitter 435*b* (and aligned with the distal-tip optically-transparent region 470*b*). Additionally, the embodiment illustrated in FIG. 4 shows one of the sensing electrodes formed as a transparent material disposed along the segmented optically-transparent region 470*a*. It will be understood that, in various embodiments, an optical stimulation lead assembly can include one or more sensing electrodes disposed at any suitable location along one or more optical fibers, the lead body, one or more optically-transparent regions, or any combination thereof.

In some embodiments, the number of sensing electrodes of a lead assembly is equal to the number of light emitters. In some embodiments, the number of sensing electrodes of a lead assembly is greater than the number of light emitters. In other embodiments, the number of sensing electrodes of a lead assembly is fewer than the number of light emitters.

The light emitter(s) and sensing electrode(s) can be disposed on any implantable lead suitable for emitting light and sensing electrical activity. In the embodiment illustrated in FIG. 4, the light emitter(s) and sensing electrode(s) are shown disposed along a percutaneous lead. It will be understood that the light emitter(s) and sensing electrode(s) can be disposed along other types of lead including, for example, paddle lead, cuff leads, or the like. FIG. 4 shows a single lead. It will be understood that an optical stimulation system can include multiple leads, with at least one light emitter disposed along each of the leads. In some instances, a sensing electrode disposed along a first lead may sense electrical activity in response to stimulation from a second lead.

The optical lead system 400 includes a control interface 455 coupled to the processor 404. The control interface 455 displays various parameters of the lead before stimulation, during stimulation, or both. The control interface 455 also enables a user to control one or more stimulation parameters. In at least some embodiments, user-selected changes to one or more of the stimulation parameters are reflected in the displayed activation volumes. In some embodiments, the control interface 455 generates and displays estimated activation volumes. In at least some embodiments, the control interface 455 receives information from the feedback subsystem 450 (e.g., sensed electrical signals received from the one or more sensing electrodes).

In at least some embodiments, the optical lead system 400 determines which light emitters are emitting light at an excitatory wavelength, which light emitters are emitting light at an inhibitory wavelength, and which emitters are not emitting light at an activation wavelength (or are not emitting light at all). In some embodiments, the optical lead system 400 may be able to determine one or more stimulation parameters for one or more of the light emitters, such as intensity, pulse frequency, pulse width, wavelength, cycling, electrode stimulation configuration, or combinations thereof. In at least some embodiments, a desired activation volume can be used to estimate changes in stimulation parameters needed to obtain the desired activation volume.

Turning to FIGS. 6A-6G, when an array of light emitters is emitting light into a target stimulation location that contains neurons that, in turn, contain genetic agents for exciting or inhibiting those neurons (or both), the sizes or shapes (or both) of activation volumes may be affected by how many of the light emitters are inhibiting emitters, exciting emitters, or turned off (or emitting light at a non-activating wavelength, or emitting light at a sub-threshold intensity, or the like). In some instances, both excitatory and inhibitory genetic agents are introduced into the same neurons. In which case, selectively switching between an excitatory range of wavelengths and an inhibitory range of wavelengths (i.e., programming an emitter to switch between functioning as an exciting emitter or functioning as an inhibiting emitter) can steer stimulation. It may be advantageous to be able to steer stimulation to fine-tune therapy. It will be understood that different disease/pain etiologies may require different stimulation parameters for generating effective therapy.

FIGS. 6A-6G show a distal portion of a lead 603 with five light emitters disposed along the lead in three levels (i.e., axial positions along the longitudinal length of the lead). It will be understood that the lead can be arranged with any suitable number of light emitters (e.g., one, two, three, four, five, six, seven, eight, nine, ten, eleven, twelve, fourteen, sixteen, eighteen, twenty, thirty, or more), with any suitable number of levels (e.g., one, two, three, four, five, six, seven, eight, or more), and with any suitable number of light emitters positioned along each level (e.g., one, two, three, four, five, or more). In at least some embodiments, at least one ring-shaped light emitter can be utilized, where the light emitter is capable of emitting light around the entire circumference of the lead via, for example, rotation of the light emitter (or a mirror). In the embodiments illustrated in FIGS. 6A-6E, the five light emitters are arranged into a proximal-most (along the length of the lead) set of light emitters, an intermediately-positioned (along the length of the lead) set of light emitters, and a distal-tip light emitter (i.e., at the distal tip of the lead).

Figure 6A:
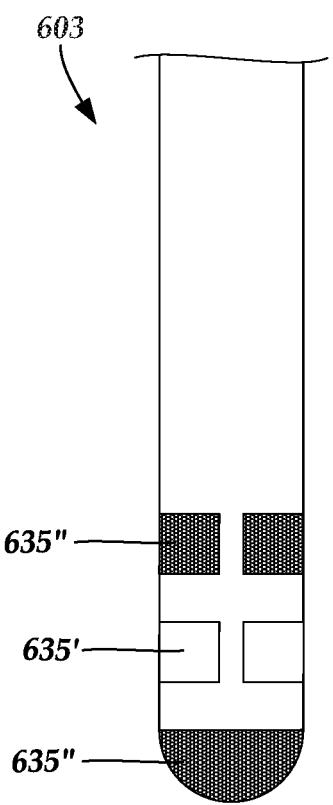
FIGS. 6A-6G are schematic side views of various embodiments of a distal portion of a lead with different combinations of exciting light emitters, inhibiting light emitters, and light emitters that are turned off, according to the invention.
Figure 6B:
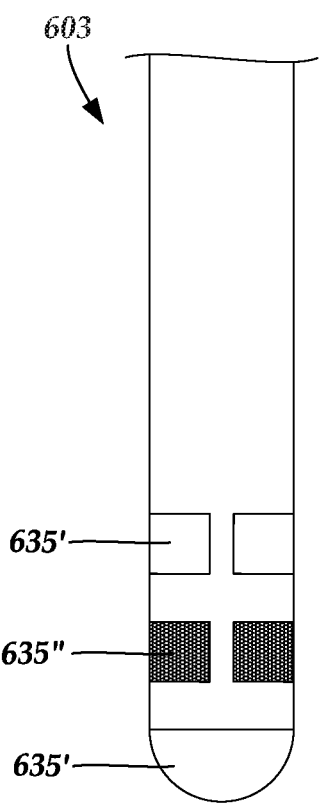

In at least some embodiments, each light emitter along a given level is either an exciting emitter or an inhibiting emitter. FIG. 6A shows the proximal-most set of light emitters functioning as exciting emitters 635", the intermediately-positioned light emitters functioning as inhibiting emitters 635', and the distal-tip light emitter functioning as an exciting emitter 635". FIG. 6B shows the proximal-most set of light emitters functioning as inhibiting emitters 635', the intermediately-positioned light emitters functioning as exciting emitters 635", and the distal-tip light emitter functioning as an inhibiting emitter 635'.

Figure 6C:
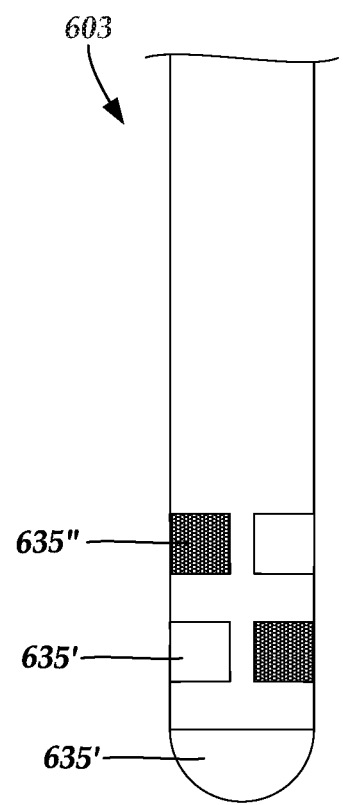
Figure 6D:
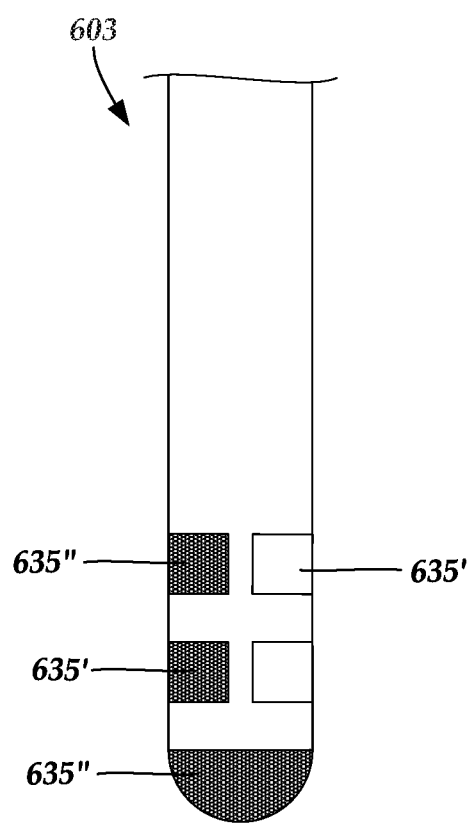

In at least some embodiments, each level that includes multiple light emitters includes both an exciting emitter and an inhibiting emitter. FIG. 6C shows one of the proximal-most set of light emitters functioning as an inhibiting emitter 635' and the other of the proximal-most light emitters functioning as an exciting emitter 635". Likewise, one of the intermediately-positioned light emitters functioning as an inhibiting emitter 635' and the other of the intermediately-positioned light emitters functioning as an exciting emitter 635". The distal-tip light emitter functioning as an inhibiting emitter 635'. FIG. 6D shows one of the proximal-most set of light emitters functioning as an inhibiting emitter 635' and the other of the proximal-most light emitters functioning as an exciting emitter 635". Likewise, one of the intermediately-positioned light emitters functioning as an inhibiting emitter 635' and the other of the intermediately-positioned light emitters functioning as an exciting emitter 635". The distal-tip light emitter functioning as an exciting emitter 635".

Figure 6E:
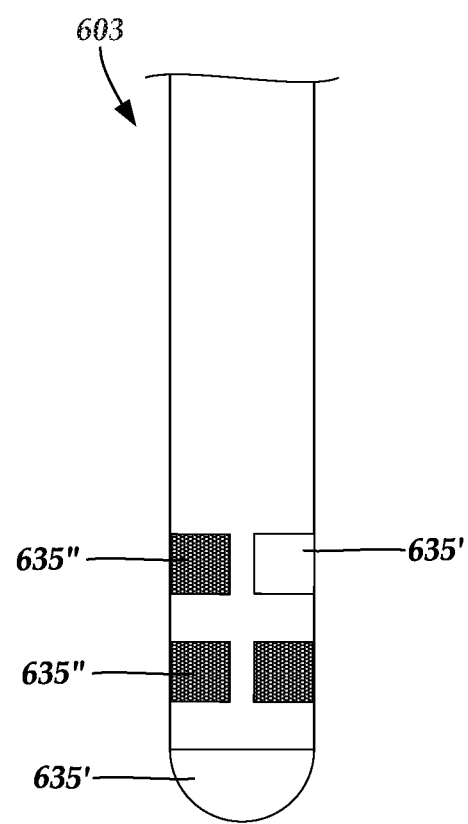

In at least some embodiments, when there are multiple levels with multiple light emitters each, at least one level includes both an exciting emitter and an inhibiting emitter and at least one level includes all exciting members or all inhibiting members. FIG. 6E shows one of the proximal-most set of light emitters functioning as an inhibiting emitter 635' and the other of the proximal-most light emitters functioning as an exciting emitter 635". Each of the intermediately-positioned light emitters functioning as an exciting emitter 635". The distal-tip light emitter functioning as an inhibiting emitter 635'.

Figure 6F:
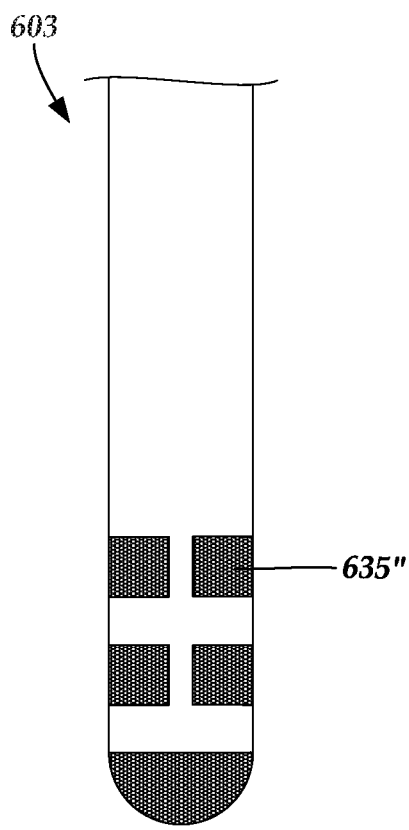

In at least some embodiments, all of the light emitters functioning as either exciting emitters or inhibiting emitters. FIG. 6F shows all of the light emitters functioning as exciting emitters 635".

Figure 6G:
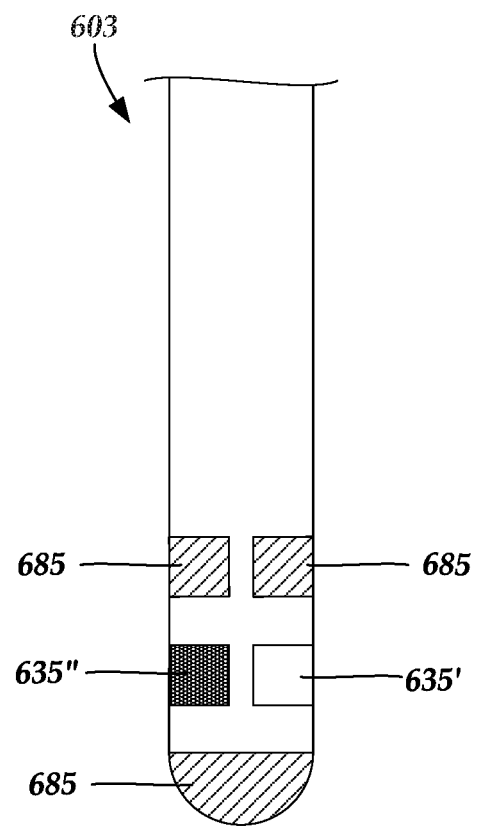

In at least some embodiments, one or more of the light emitters can be turned off. FIG. 6G shows one of the intermediately-positioned light emitters functioning as an inhibiting emitter 635' and the other of the intermediately-positioned light emitters functioning as an exciting emitter 635", while the proximal-most light emitters and the distal-tip light emitter are turned off 685. It will be understood that, in at least some embodiments, any of the light emitters can be turned off individually, or along a particular radial positioning along the circumference of the lead, or along a particular level (i.e., axial position along the longitudinal length of the lead).

Figure 7A:
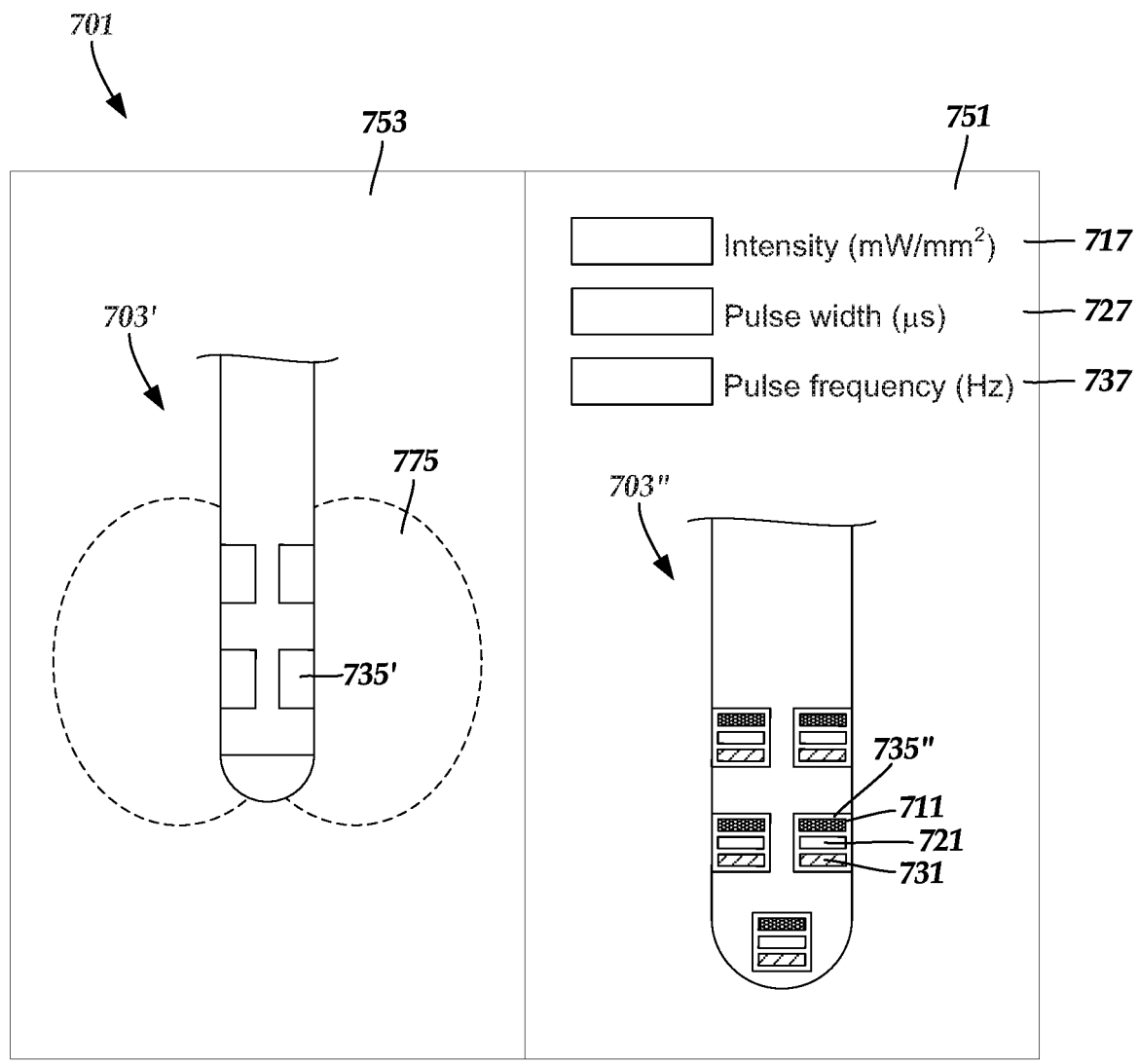
FIG. 7A is a schematic view of one embodiment of a graphical display of a lead with light emitters and user options for selecting stimulation parameters for the light emitters, according to the invention.

Turning to FIG. 7A, the control interface 455 enables a user to adjust at least one stimulation parameter of at least one light emitter of a lead. The control interface 455 may also enable a user to view a graphical representation of the lead and the light emitters. In some embodiments, a single set of stimulation parameters is selected for all light emitters of the lead. In some embodiments, a separate set of stimulation parameters is individually selected for each light emitter of the lead. In at least some embodiments, light-emitter stimulation parameters are adjustable either universally or individually.

FIG. 7A shows a display 701 that includes an input portion 751 and a visualization portion 753. The input portion 751 includes one or more user-selectable controls for selecting stimulation parameters and the visualization portion 753 includes a graphical representation of a lead 703' (i.e., virtual lead 703') disposed within a graphical representation of a target stimulation locations 775 (i.e., virtual target stimulation location 775).

Optionally, the virtual target stimulation location can be set to be excitatory or inhibitory (or both), as desired, to correspond to an actual implantation procedure. In the illustrated embodiment, the virtual target stimulation location 775 represents a region where both excitatory and inhibitory genetic agents were introduced into neurons. Accordingly, neurons within the virtual target stimulation location 775 can exhibit either an inhibitory response or an excitatory response when activated, depending on the wavelengths of emitted light.

Graphical representations of light emitters (i.e., virtual light emitters), such as virtual light emitter 735', are disposed along the virtual lead 703'. The number and positioning of the virtual light emitters can vary, as desired, to correspond to the number and positioning of light emitters disposed on/in an actual lead implanted (or to be implanted) into a patient.

The virtual light emitters can be represented by any suitable shape. In at least some embodiments, the virtual light emitters are represented as geometric shapes (e.g., rectangles, circles, ovals, or the like). In some embodiments, each virtual light emitter is individually recognizable by its relative positioning along the virtual lead.

The input portion 751 includes a set of multiple stimulation parameters for which a user can set values. In the illustrated embodiment, the stimulation parameters include intensity 717, pulse width 727, and pulse frequency 737. In some instances, the input portion 751 may include one or more preset (e.g., default) values to choose between, or a finite range of values for a user to choose from for each particular stimulation parameter. In the illustrated embodiment, each stimulation parameter includes an input field for a user to enter a desired value. In at least some embodiments, particular values for each of the different options 717, 727, 737 can be set and toggled between, as desired.

In at least some embodiments, the input portion 751 also includes a virtual lead (i.e., a second virtual lead 703") with graphical representations of light emitters (i.e., virtual light emitters), such as virtual light emitter 735". Each of the virtual light emitters disposed along the second virtual lead 703" has three different settings to choose between: excitatory 711, inhibitory 721, and OFF 731. Selecting between each of the options 711, 721, 731 effectively selects the wavelength of emitted light, with excitatory 711 including at least one wavelength within the band of wavelengths causing an excitatory response within the neurons of interest, inhibitory 721 including at least one wavelength within the band of wavelengths causing an inhibitory response within the neurons of interest, and OFF 731 preventing light from being emitted from the light emitter. Optionally, OFF 731 can enable light to be emitted that is exclusively outside of the band of wavelengths that cause an excitatory response and the band of wavelengths that cause an inhibitory response, or is emitted at an intensity that is below a threshold intensity needed to excite or inhibit the neurons of interest. In at least some embodiments, the different options 711, 721, 731 can be toggled between by a user, as desired.

Figure 7B:
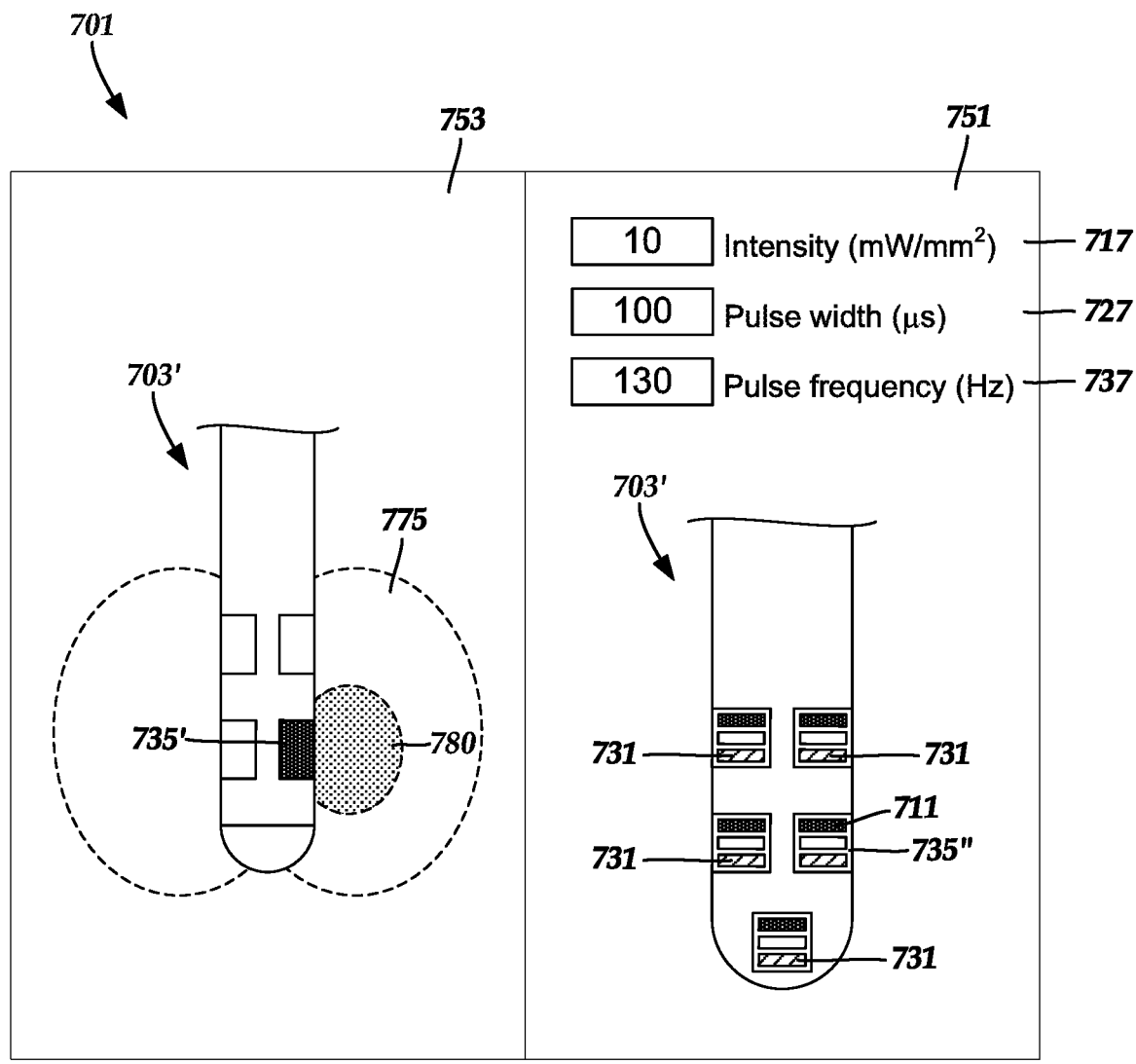
FIG. 7B is a schematic view of one embodiment of the graphical display of FIG. 7A with an exemplary set of selected stimulation parameters, according to the invention.

Turning to FIG. 7B, in at least some embodiments the control interface 455 displays one or more graphical representations of activation volume(s) (i.e., virtual activation volume(s)) positioned around virtual light emitters. FIG. 7B shows the display 701 after an exemplary set of stimulation parameters is input into the input portion 751. In FIG. 7B, user-selected values are shown for each of the stimulation parameters 717, 727, 737.

FIG. 7B also shows one of the virtual light emitters 735" of the input portion 751 set to the excitatory wavelength 711, while the remaining virtual light emitters are set to OFF 731. The virtual lead 703' of the visualization portion 753 shows a virtual activation volume 780 within the virtual target stimulation location 775 and positioned about the corresponding virtual light emitter 735' selected in the input portion 751.

In the case of wavelength, different wavelengths can be used to control whether an activated neuron is producing an excitatory response or an inhibitory response to stimulation. In some instances, the control interface 455 may enable toggling between two or more wavelengths that may elicit a difference activation response from the same neurons. For example, as mentioned above, selectively switching between an excitatory range of wavelengths and an inhibitory range of wavelengths can be used to elicit either an excitatory response or an inhibitory response from those neurons.

In at least some embodiments, the estimated size and shape of the virtual activation volume(s) corresponds to the user-selected values for the stimulation parameters. In at least some embodiments, the virtual activation volume(s) can alternately, or additionally, be based on information received from the sensing electrodes of the actual lead assembly, via the feedback subsystem 450 (e.g., sensing of a new electrical signal, sensing a change in the amount or quality of an electrical signal, the disappearance of an electrical signal, or the like).

The virtual activation volumes may also take into account known properties of light and the local environment through which the light travels from the actual lead to the target stimulation location(s). For example, the virtual activation volumes may take into account the Beer-Lambert law (relating to the attenuation of light to the properties of the material through which the light is traveling). Additionally, the virtual activation volumes may also take into account light scattering, as exemplified by scattering laws, such as Rayleigh scattering, Mie scattering, and the like. Other light properties taken into account may include, for example, reflection, refraction, dispersion, interference, diffraction, polarization, diffusion, absorption, or the like.

Figure 8:
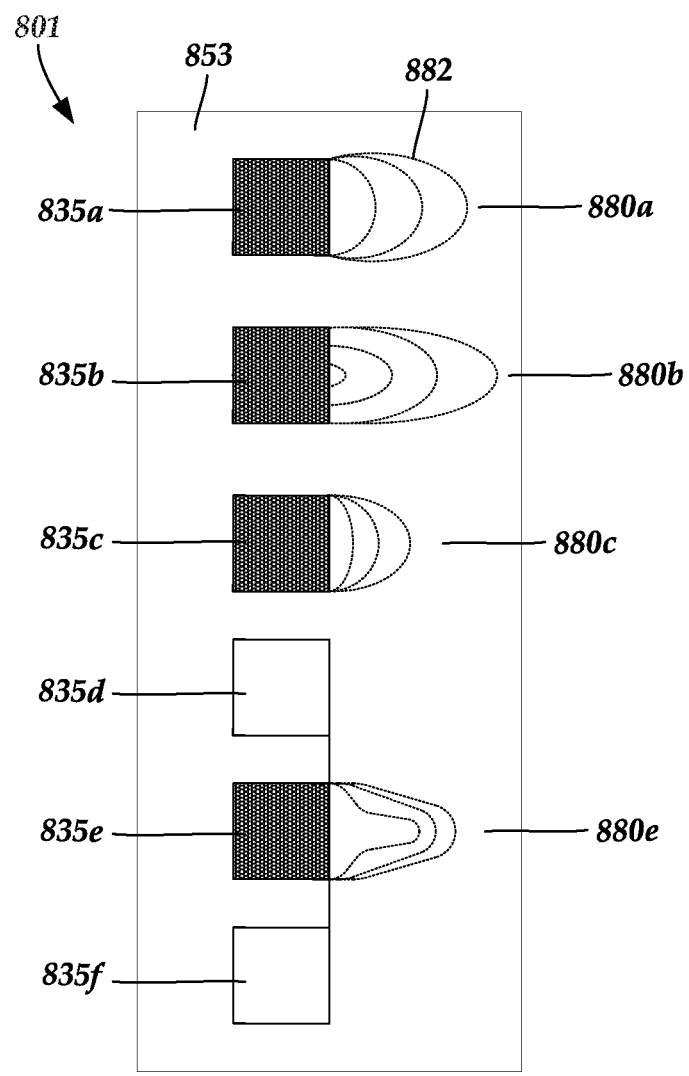
FIG. 8 is a schematic view of one embodiment of a graphical display of several different activation-field contours extending from virtual light emitters based on different stimulation parameters, according to the invention.

Turning to FIG. 8, in some embodiments the control interface 455 adjusts the size or shape (or both) of the virtual activation volume(s) positioned around the virtual representations of the light emitters in the visualization portion of the display in response to user-selected values for the stimulation parameters. Adjusting the contours of the activation volumes can affect the number of neurons that are activated, as well as which particular neurons are activated within a target stimulation location. Thus, providing a visualization of the size or shape (or both) of an activation volume for a given set of stimulation parameters may facilitate the fine-tuning of therapy.

FIG. 8 shows a visualization portion 853 of a display 801 that includes virtual light emitters 835a, 835b, 835c, 835d, 835e, 835f. The virtual light emitters can be displayed with or without a virtual lead. Virtual light emitters 835a, 835b, 835c, and 835e are excitatory and have activation volumes 880a, 880b, 880c, and 880e, respectively, extending therefrom. Below is one narrow example showing some possible ways of showing how the virtual activation volumes can be displayed to enable a user to select a particular size and shape of an activation volume by selecting different stimulation parameters.

In the embodiment illustrated in FIG. 8, the activation volume 880a represents a default setting, where the pulse frequency is 40 Hz and the pulse width is 100 μs. Each of the contours, such as contour 882, represents different potential outer boundaries of the activation volume at a particular number of spikes per second (e.g., the innermost contour corresponding to 40 spikes per second, the adjacent contour corresponding to 20 spikes per second, and the outermost contour corresponding to 10 spikes per second). Note that, spikes/second is a figure that denotes neuronal activation. Neuronal electrical activity, or neuronal firing, is the overall neuron response that is the cumulative effect of many actions potentials. Each action potential or combination of action potentials (if the electrode is not small enough and cannot distinguish between action potentials) can be considered a spike.

In the embodiment illustrated in FIG. 8, the activation volume 880b represents a change in pulse width from the default activation volume 880a. The activation volume 880b has a pulse frequency of 40 Hz and a pulse width of 500 μs. The contours for the activation volume 880b are, for example, 80 spikes per minute for the innermost contour, 40 spikes per second for the adjacent contour, 20 spikes per second for the next adjacent contour, and 10 spikes per second for the outermost contour.

In the embodiment illustrated in FIG. 8, the activation volume 880c represents a change in pulse frequency from the default activation volume 880a. The activation volume 880c has a pulse frequency of 20 Hz and a pulse width of 100 μs. The contours for the activation volume 880c are, for example, 20 spikes per minute for the innermost contour, 10 spikes per second for the adjacent contour, and 5 spikes per second for the outermost contour.

In the embodiment illustrated in FIG. 8, the activation volume 880e represents the added effect of inhibitory stimulation from flanking light emitters 835d and 835f. The contours for the activation volume 880e are, for example, 40 spikes per minute for the innermost contour, 20 spikes per second for the adjacent contour, and 10 spikes per second for the outermost contour. As shown in the activation volume 880e, with the addition of flanking inhibitory stimulation the shape of the activation volume 880e narrows at it extends away from the light emitter 835d, as compared to the activation volumes 880a, 880b, 880c, due to the inhibitory stimulation of light emitters 835d, 835f.

Figure 9:
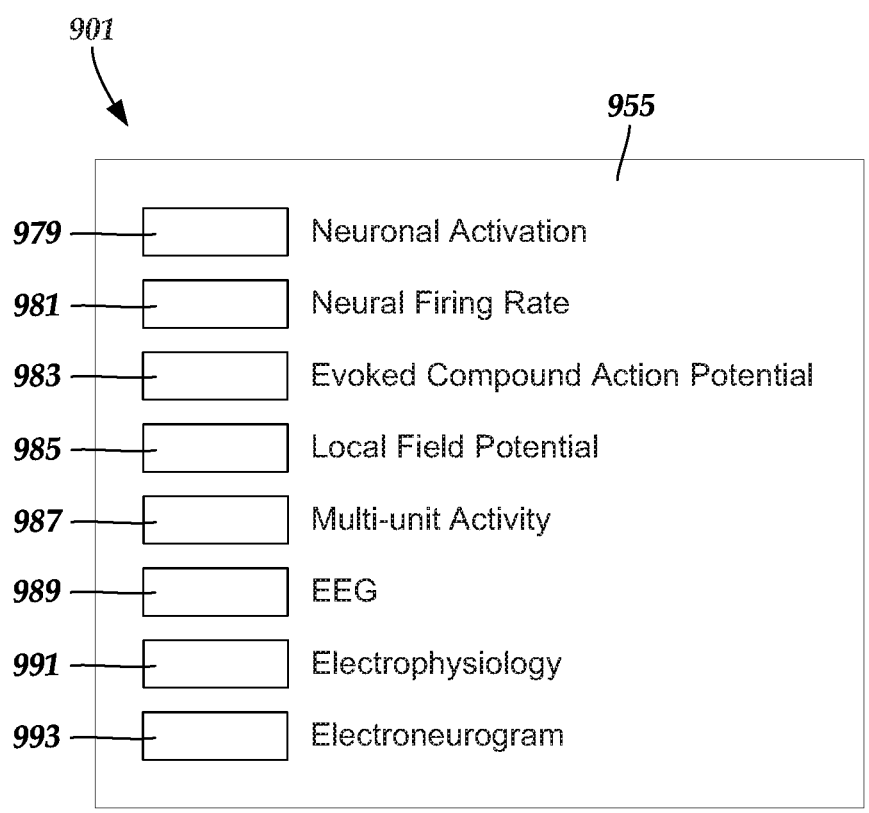
FIG. 9 is a schematic view of one embodiment of a graphical display of user-selectable options for electrical signals for sensing electrodes to sense, according to the invention.

Turning to FIG. 9, as mentioned above the estimates of the activation contours can be based, at least in part, on one or more of stimulation parameters, known principles of light, and the local environment. In some instances, the estimates of the activation contours are based, at least in part, on sensed electrical signals from the sensing electrodes of the actual lead (see e.g., FIG. 4). In at least some embodiments, the control interface enables a user to select which electrical signals are being sensed by the sensing electrodes.

FIG. 9 shows a sensing portion 955 of a display 901 that includes one or more different electrical signals that a user can select between for determining which electrical signal are being detected by one or more actual sensing electrodes disposed on/in an actual lead. In the illustrated embodiment, electrical signals include options for direct sensing of electrical activity of neurons: neuronal activation 979; and neuronal firing rates 981. Additionally, the illustrated embodiment includes detectable surrogate signals that can be used to indirectly determine one or more of neuronal activation, neuronal response, or neuronal firing rates. The illustrated surrogate signals include evoked compound action potentials 983, local field potentials 985, multi-unit activity signals 987, electroencephalogram signals 989, electrophysiology signals 991, and electroneurogram signals 993. Other surrogate signals are possible.

In at least some embodiments, when both excitatory and inhibitory neurons are introduced into neurons within a target stimulation location the control interface 455 can determine a net effect of stimulation. The net effect of stimulation can be determined by comparing, for a determined location, the relative intensity of light emitted having wavelengths that generate excitatory activation to the relative intensity of light emitted having wavelengths that generate inhibitory activation. In at least some embodiments, the net effect of stimulation can be determined using fractionalizations.

The control interface 455 includes one or more controllers (e.g., buttons, switches, knobs, levers, toggles, or the like) that enable a user to select stimulation parameters, or select which sensed electrical signals are being recorded. The controllers can be implemented in any suitable way, such as mechanically (e.g., toggles, knobs, switches, levers, or the like or combinations thereof) or electronically (e.g., a touch screen or display screen coupled to a mouse, touch pad, keyboard, or the like or combinations thereof). In some embodiments, the control interface 455 can determine the location of the neurons emitting the sensed electrical signal. In some embodiments, the control interface 455 can determine which light emitter emitted the light that stimulated the neuron emitting the sense electrical signal.

Selection, by a user, of one or more stimulation parameters in the input portion 751 causes the actual lead to emit light at the selected stimulation parameters. Selection of one of the settings 717, 727, 737, 711, 721, 731 can cause an immediate action in the actual lead. Alternatively, selection of one of the settings 711, 721, 731 can cause a future action based on an amount of time, another action, a threshold being exceeded, or the like. In at least some embodiments, the actual lead does not implement the input settings until after the input settings are displayed on the visualization portion 753 and a user confirms implementation of those selections (e.g., clicking a confirmation indicator, or the like).

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each of the methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An optical stimulation system, comprising:
    an optical stimulation lead comprising
        a lead body having a distal portion and a proximal portion, and
        a plurality of light emitters disposed along the distal portion of the lead body and configured and arranged to emit light having wavelengths that activate light-sensitive neurons within a target stimulation location, the light-sensitive neurons generating either an excitatory response or an inhibitory response when activated depending on the wavelength of the emitted light;
    a control module coupleable to the optical stimulation lead, the control module configured and arranged to direct the emission of light from the plurality of light emitters using a set of stimulation parameters; and
    a control interface communicatively coupleable to the control module, the control interface comprising a plurality of user-selectable controls to adjust stimulation parameters of the set of stimulation parameters, wherein the user-selectable controls comprise a graphical representation of a light emitter for each of the plurality of light emitters, wherein each graphical representation comprises one or more user-selectable emitter controls to indicate whether that light emitter emits light and, if so, whether the emitted light comprises a first wavelength that generates an excitatory response from activated light-sensitive neurons, or a second wavelength that generates an inhibitory response from activated light-sensitive neurons.

2. The optical stimulation system of claim 1 wherein, for each graphical representation, the corresponding one or more user-selectable emitter controls enable a user to switch between selecting that the light emitter emits light that generates an excitatory response from activated light-sensitive neurons, and selecting that the light emitter emits light that generates an inhibitory response from activated light-sensitive neurons.

3. The optical stimulation system of claim 1, wherein the control interface displays a graphical representation of the optical stimulation lead.

4. The optical stimulation system of claim 3 wherein, for each graphical representation, the graphical representation of the light emitter is disposed along the graphical representation of the optical stimulation lead.

5. The optical stimulation system of claim 4, wherein the control interface is configured and arranged to display a graphical representation of an activation volume based on user selection of the light emitters, the graphical representation of the activation volume depicting an estimated region where emitted light from the optical stimulation lead is sufficient to activate the light-sensitive neurons.

6. The optical stimulation system of claim 5, wherein a size and shape of the graphical representation of the activation volume is based, at least in part, on at least one stimulation parameter of the set of stimulation parameters.

7. The optical stimulation system of claim 6, wherein the optical stimulation lead further comprises a sensing electrode disposed along the distal portion of the lead body and coupleable to the control module, the sensing electrode configured and arranged to sense electrical activity from the light-sensitive neurons.

8. The optical stimulation system of claim 7, wherein the sensing electrode is configured and arranged to sense electrical activity from the light-sensitive neurons during activation of the light-sensitive neurons.

9. The optical stimulation system of claim 7, wherein the sensing electrode is configured and arranged to sense changes in electrical activity from the activated light-sensitive neurons in response to the emitted light.

10. The optical stimulation system of claim 7 wherein, for each of the graphical representations of activation volumes, the size and shape of that graphical representation of the activation volume is based, at least in part, on sensed electrical activity from the light-sensitive neurons received from the sensing electrode.

11. The optical stimulation system of claim 10, wherein the control interface comprises a user-selectable control for selecting which type of electrical activity from the light-sensitive neurons is sensed by the sensing electrode.

12. The optical stimulation system of claim 11, wherein the sensing electrode is configured and arranged to sense at least one of a level of neuronal activation or neuronal firing rate of the light-sensitive neurons in response to the emitted light.

13. The optical stimulation system of claim 11, wherein the sensing electrode is configured and arranged to sense at least one surrogate electrical signal from the light-sensitive neurons in response to the emitted light, the the at least one surrogate electrical signal usable for determining at least one of a level of neuronal activation or neuronal firing rate of the light-sensitive neurons in response to the emitted light.

14. The optical stimulation system of claim 13, wherein the at least one surrogate electrical signal comprises one of evoked compound action potential, local field potential, a multiunit activity signal, an electroencephalogram signal, an electrospinogram signal, an electrophysiology signal, an electrospinogram signal, or an electroneurogram signal.

15. The optical stimulation system of claim 1, wherein the set of stimulation parameters comprises at least one of intensity, pulse width, pulse frequency, cycling, or electrode stimulation configuration.

16. A method for optically stimulating a patient, the method comprising:
advancing the optical stimulation lead of the optical stimulation system of claim 1 in proximity to a target stimulation location within the patient, the target stimulation location containing light-sensitive neurons, the light-sensitive neurons generating either an excitatory response when activated by light of a first wavelength, or an inhibitory response when activated by light of a second wavelength;
selecting, for each light emitter of the plurality of light emitters of the optical stimulation lead, whether that light emitter emits light and, if so, whether the emitted light comprises the first wavelength or the second wavelength;
selecting at least one stimulation parameter of the set of stimulation parameters displayed by the control interface of the optical stimulation system; and
emitting light towards the target stimulation location from each light emitter of the plurality of light emitters selected to emit light.

17. The method of claim 16, wherein selecting at least one stimulation parameter of the set of stimulation parameters comprises selecting at least one of intensity, pulse width, pulse frequency, cycling, or electrode stimulation configuration.

18. The method of claim 16, wherein selecting at least one stimulation parameter of the set of stimulation parameters comprises selecting at least one stimulation parameter based, at least in part, on a size and shape of a graphical representation of an activation volume displayed on the control interface of the optical stimulation system.

19. The method of claim 16, wherein selecting at least one stimulation parameter of the set of stimulation parameters comprises selecting at least one stimulation parameter based, at least in part, on sensed electrical activity from the light-sensitive neurons.

20. The method of claim 19, wherein selecting at least one stimulation parameter based, at least in part, on sensed electrical activity from the light-sensitive neurons comprises selecting which type of electrical signals are sensed.

* * * * *